US011136615B2

United States Patent
Shi et al.

(10) Patent No.: US 11,136,615 B2
(45) Date of Patent: Oct. 5, 2021

(54) COMPOSITIONS AND METHODS FOR STABILIZING BENZOTHIAZOLE LUCIFERIN ANALOGS

(71) Applicant: PROMEGA CORPORATION, Madison, WI (US)

(72) Inventors: Ce Shi, San Luis Obispo, CA (US); Mary P. Hall, Waunakee, WI (US); Thomas A. Kirkland, Atascadero, CA (US); Lance P. Encell, Fitchburg, WI (US); Poncho Meisenheimer, San Luis Obispo, CA (US); Wenhui Zhou, San Luis Obispo, CA (US)

(73) Assignee: PROMEGA CORPORATION, Madison, WI (US)

( * ) Notice: Subject to any disclaimer, the term of this patent is extended or adjusted under 35 U.S.C. 154(b) by 154 days.

(21) Appl. No.: 16/053,413

(22) Filed: Aug. 2, 2018

(65) Prior Publication Data

US 2019/0040449 A1 Feb. 7, 2019

Related U.S. Application Data

(60) Provisional application No. 62/541,350, filed on Aug. 4, 2017.

(51) Int. Cl.
*C12Q 1/66* (2006.01)
*C07D 253/06* (2006.01)
*C07D 417/04* (2006.01)

(52) U.S. Cl.
CPC .............. *C12Q 1/66* (2013.01); *C07D 253/06* (2013.01); *C07D 417/04* (2013.01)

(58) Field of Classification Search
CPC .............. C07D 253/075; C07D 277/84; C07D 417/14; C07D 417/04; C07D 513/04; C07D 513/14; C07D 513/22; C07D 253/06; C12Q 1/66; A61K 31/53
USPC .......... 544/182; 514/243, 366, 150; 548/150, 548/100
See application file for complete search history.

(56) References Cited

U.S. PATENT DOCUMENTS

| 5,098,828 | A | 3/1992 | Geiger et al. |
| 7,692,022 | B2 | 4/2010 | Cali et al. |
| 7,910,087 | B2 | 3/2011 | Miller |
| 9,447,450 | B2 * | 9/2016 | Hitko .................. C07D 417/04 |
| 9,487,814 | B2 | 11/2016 | Valley et al. |
| 9,732,373 | B2 * | 8/2017 | Encell .................. C12N 9/0069 |
| 9,868,977 | B2 * | 1/2018 | Hitko .................. C07D 417/04 |
| 2007/0015790 | A1 | 1/2007 | Cali et al. |
| 2014/0304842 | A1 | 10/2014 | Hitko et al. |
| 2018/0155762 | A1 | 6/2018 | Encell et al. |

FOREIGN PATENT DOCUMENTS

| JP | 4478231 B2 | 6/2000 |
| JP | 4379644 B2 | 9/2000 |
| JP | 4503724 B2 | 7/2010 |
| JP | 2014039486 A | 3/2014 |
| WO | WO2001020002 | 3/2001 |
| WO | WO2001096862 | 12/2001 |
| WO | WO2006013837 | 2/2006 |
| WO | WO 2006130551 | 5/2006 |
| WO | WO 2014159044 | 10/2014 |
| WO | WO 2015179864 A1 | 11/2015 |
| WO | WO2017057672 | 4/2017 |

OTHER PUBLICATIONS

Liu et al., "Design, synthesis, and biological evaluation of 7H-thlazolo[3,2-b]-1,2,4-triazin-7-one derivatives as novel acetylcholinesterase inhibitors," ARKIVOC (2009) 333-348.

Liu et al., "Design, Synthesis, and Biological Evaluation of 7H-thiazolo[3,2-b]-1,2,4-triazin-7-one Derivatives as Acetylcholinesterase Inhibitors," *Letters in Drug Design and Discovery* (2010) 7:5-8.

Sun et al., "D-Luciferin Analogues: a Multicolor Toolbox for Bioluminescence Imaging." Angewandte Chemie International Edition Jul. 13, 2012. 51(34): 8428-8430.

International Search Report and Written Opinion dated Nov. 13, 2018 for PCT/US2018/045040, 14 pages.

\* cited by examiner

*Primary Examiner* — Kahsay Habte
(74) *Attorney, Agent, or Firm* — Casimir Jones, S.C.

(57) ABSTRACT

Disclosed herein are compositions and methods for stabilizing a benzothiazole luciferin analog such as D-luciferin and 6-amino-D-luciferin. The compositions may include the benzothiazole luciferin analog, a thionucleobase compound of formula (I), and a liquid medium, in which the thionucleobase is present in an amount effective to stabilize the luminogenic composition against decomposition. The methods provided herein may stabilize the benzothiazole luciferin analog against decomposition by contacting the benzothiazole luciferin analog with an effective amount of the thionucleobase compound in the presence of a liquid medium. Also provided herein is a kit containing the composition.

31 Claims, 6 Drawing Sheets

D-luciferin

Dehydroluciferin

| Substituents | Luciferin |
|---|---|
| 5'-H, 6-OH | H-LH2 |
| 5'-H, 6-NH$_2$ | NH2-LH2 |

2-hydroxyethyl ester of luciferin methyl ether proluciferin1

US 11,136,615 B2

COMPOSITIONS AND METHODS FOR STABILIZING BENZOTHIAZOLE LUCIFERIN ANALOGS

CROSS-REFERENCE TO RELATED APPLICATIONS

This application claims priority to U.S. Provisional Patent Application No. 62/541,350, filed on Aug. 4, 2017, the entire content of which is incorporated herein by reference.

TECHNICAL FIELD

The present invention relates to compositions and methods for stabilizing benzothiazole luciferin analogs.

BACKGROUND

Luminescence is often used in biological assays as a measure of the activity of a reporter molecule. The reporter molecule, in turn, links the luminescent measurement to a biological process of interest such as transcription (gene expression), translation (protein expression), protein-protein interactions, and so forth, thereby allowing for quantitative measurements of changes occurring in the biological process.

The reporter molecule is typically a luminogenic enzyme (e.g., firefly luciferase, Renilla luciferase, Oplophorus luciferase, etc.) that, when provided with its luminogenic substrate, results in the production of light, i.e., luminescence. The luminogenic substrate (e.g., a luciferin), however, can decompose during storage, thereby resulting in loss of the substrate before addition to or use in the biological assay. Such decomposition can be the result of the instability of the luminogenic substrate in solution over time in a temperature-dependent manner. This decomposition results in a waste of the luminogenic substrate and reduced sensitivity and reproducibility of luminescent measurements derived from biological assays that employed the decomposed luminogenic substrate. Additionally, the products from this decomposition often inhibit the luminescent reaction.

D-luciferin is the natural substrate for firefly and click beetle luciferases. Luciferins and luciferin derivatives are thermally unstable when stored in solutions or moist environment at ambient temperature over time. Dehydroluciferins have been identified as the major breakdown products, which are potent inhibitors of luciferases and lead to decreased and inconsistent light output performance. Pro-luciferin analogs are widely used in analyte-dependent, firefly luciferase-based assay systems. Similarly to luciferins, the decomposition to the corresponding pro-dehydroluciferin analogs also affects the luminescence performance negatively. It is desirable to have methods to reduce the formation of breakdown products, especially for applications that require luciferins or luciferin derivatives to be stored in solutions at above ambient temperature over long period of time.

Accordingly, the need exists for the identification and development of new compositions and/or methods for stabilizing a luminogenic substrate prior to its use in a luminescent reaction.

SUMMARY

The present disclosure provides a composition comprising: (a) a benzothiazole luciferin analog, or a salt thereof; (b) an effective amount of a compound of formula (I) or a tautomer thereof,

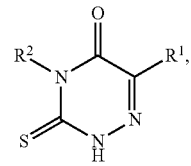

wherein
R[1] is hydrogen, optionally substituted alkyl, optionally substituted arylalkyl, optionally substituted heteroarylalkyl, optionally substituted cycloalkyl, optionally substituted aryl, optionally substituted heteroaryl, carboxylic acid, ester, $NR^aR^b$, optionally substituted imine, hydroxyl, or oxo;
R[2] is hydrogen, $NR^aR^b$, optionally substituted imine, optionally substituted alkyl, or optionally substituted aryl;
$R^a$ and $R^b$, at each occurrence, are each independently hydrogen, optionally substituted alkyl, or optionally substituted aryl; and
(c) optionally, a liquid medium.

The present disclosure also provides a kit comprising the components of the above composition.

The present disclosure further provides a method for stabilizing a benzothiazole luciferin analog, the method comprising contacting the benzothiazole luciferin analog, or a salt thereof, with an effective amount of a compound of formula (I) or a tautomer thereof, whereby the benzothiazole luciferin analog, or salt thereof, is stabilized against decomposition, wherein the compound of formula (I) is

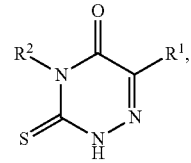

wherein
R[1] is hydrogen, optionally substituted alkyl, optionally substituted arylalkyl, optionally substituted heteroarylalkyl, optionally substituted cycloalkyl, optionally substituted aryl, optionally substituted heteroaryl, carboxylic acid, ester, $NR^aR^b$, optionally substituted imine, hydroxyl, or oxo;
R[2] is hydrogen, $NR^aR^b$, optionally substituted imine, optionally substituted alkyl, or optionally substituted aryl; and
$R^a$ and $R^b$, at each occurrence, are each independently hydrogen, optionally substituted alkyl, or optionally substituted aryl.

DETAILED DESCRIPTION

Figure 1:
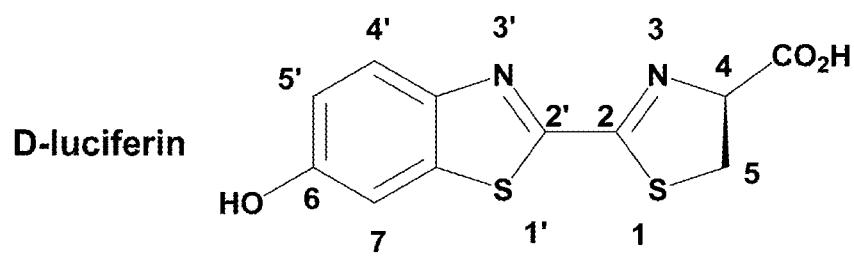
FIG. 1 shows the structures of D-luciferin and dehydroluciferin with the numbering of ring atoms, as well as the abbreviations used herein, for certain luciferin compounds.
Figure 1:
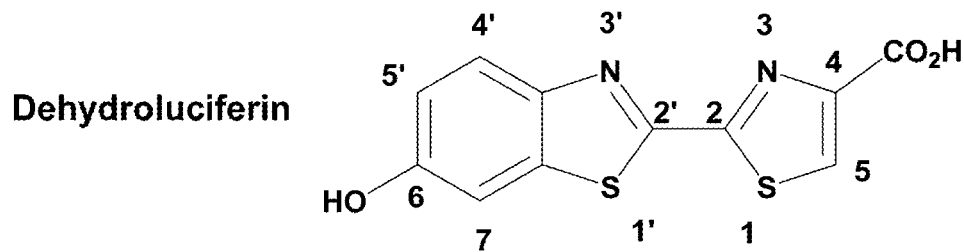

The present invention relates to a composition for stabilizing a benzothiazole luciferin analog. The benzothiazole luciferin analog includes a compound of formula (II'), or a salt thereof:

(II')

wherein is (a)

(b)

(c)

, or (d)

$R^{1'}$ is H, $C_1$-$C_4$alkyl, —$C_2$-$C_4$alkylene-OH, —$C_2$-$C_4$alkylene-O$C_1$-$C_4$alkyl, $C_3$-$C_7$cycloalkyl, aryl, benzyl or substituted benzyl, heterocyclyl, heteroaryl, or —$(CH_2)_q$—$P(Ph)_3$, wherein q is an integer selected from 1, 2, 3, 4, 5, and 6;

$R^{2'}$ is hydrogen, halogen, $C_1$-$C_4$alkyl, or $C_1$-$C_4$haloalkyl;

$R^{3'}$ is hydrogen, halogen, $C_1$-$C_4$alkyl, or $C_1$-$C_4$haloalkyl;

$R^{4'}$ is —XG or —XG$^1$;

$R^{5'}$ is hydrogen, halogen, $C_1$-$C_4$alkyl, or $C_1$-$C_4$haloalkyl;

$R^{10'}$, at each occurrence is independently halo, —$SO_3H$, $C_1$-$C_{10}$alkyl, —OH, —O($C_1$-$C_{10}$alkyl), —$NH_2$, —NH($C_1$-$C_{10}$alkyl), or —N($C_1$-$C_{10}$alkyl)($C_1$-$C_{10}$alkyl);

$R^{11'}$ is —OH, —O($C_1$-$C_{10}$alkyl), —$NH_2$, —NH($C_1$-$C_{10}$alkyl), —N($C_1$-$C_{10}$alkyl)($C_1$-$C_{10}$alkyl), —OG$^1$, —NHG$^1$, or —N($C_1$-$C_{10}$alkyl)G$^1$;

n is 0 to 5;

X is —O— or —N(G)-;

G, at each occurrence is independently H, $C_1$-$C_{12}$alkyl, or together with one of $R^{3'}$ or $R^{5'}$ forms a 5- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl); or two G together with the nitrogen atom to which they are attached form a 4- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl);

G$^1$ comprises an enzyme substrate, wherein biotransformation of the enzyme substrate by an enzyme converts G$^1$ to H; and $W^1$ and $W^2$ are each independently hydrogen, $C_1$-$C_4$alkyl, or arylalkyl; or $W^1$ and $W^2$ together with the carbon to which they are attached form a $C_3$-$C_8$cycloalkyl or a 4- to 8-membered heterocycle, the cycloalkyl and heterocycle being optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl).

In some embodiments, the benzothiazole luciferin analog of formula (II') is a compound of formula (II), or salt thereof:

(II)

wherein is (a) 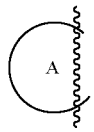

(b), (c), or (d)

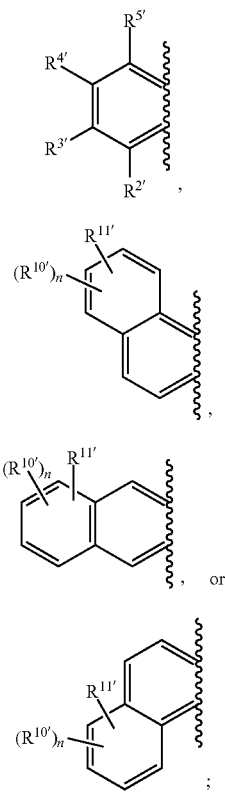

R$^{1'}$ is H, C$_1$-C$_4$alkyl, —C$_2$-C$_4$alkylene-OH, —C$_2$-C$_4$alkylene-OC$_1$-C$_4$alkyl, C$_3$-C$_7$cycloalkyl, aryl, benzyl or substituted benzyl, heterocyclyl, heteroaryl, or —(CH$_2$)$_q$—P(Ph)$_3$, wherein q is an integer selected from 1, 2, 3, 4, 5, and 6;

R$^{2'}$ is hydrogen, halogen, methyl, or trifluoromethyl;

R$^{3'}$ is hydrogen, halogen, methyl, or trifluoromethyl;

R$^{4'}$ is —XG or —XG$^1$;

R$^{5'}$ is hydrogen, halogen, methyl, or trifluoromethyl;

R$^{10'}$, at each occurrence is independently halo, —SO$_3$H, C$_1$-C$_{10}$alkyl, —OH, —O(C$_1$-C$_{10}$alkyl), —NH$_2$, —NH(C$_1$-C$_{10}$alkyl), or —N(C$_1$-C$_{10}$alkyl)(C$_1$-C$_{10}$alkyl);

R$^{11'}$ is —OH, —O(C$_1$-C$_{10}$alkyl), —NH$_2$, —NH(C$_1$-C$_{10}$alkyl), —N(C$_1$-C$_{10}$alkyl)(C$_1$-C$_{10}$alkyl), —OG$^1$, —NHG$^1$, or —N(C$_1$-C$_{10}$alkyl)G$^1$;

n is 0 to 5;

X is —O— or —N(G)-;

G, at each occurrence is independently H, C$_1$-C$_{12}$alkyl, or together with one of R$^{3'}$ or R$^{5'}$ forms a 5- to 8-membered monocyclic heterocyclic ring optionally substituted with 1-4 substituents independently selected from the group consisting of C$_1$-C$_4$alkyl, C$_1$-C$_4$haloalkyl, halo, hydroxy, oxo, and —O(C$_1$-C$_4$alkyl); or two G together with the nitrogen atom to which they are attached form a 4- to 8-membered monocyclic heterocyclic ring optionally substituted with 1-4 substituents independently selected from the group consisting of C$_1$-C$_4$alkyl, C$_1$-C$_4$haloalkyl, halo, hydroxy, oxo, and —O(C$_1$-C$_4$alkyl); and G$^1$ comprises an enzyme substrate, wherein biotransformation of the enzyme substrate by an enzyme converts G$^1$ to H.

The composition may include the benzothiazole luciferin analog, a thionucleobase, and a liquid medium. The composition may or may not include or contain a luminogenic enzyme (e.g., a luciferase).

The thionucleobase may be a compound of formula (I) or a tautomer thereof,

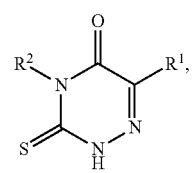

(I)

wherein

R$^1$ is hydrogen, optionally substituted alkyl, optionally substituted arylalkyl, optionally substituted heteroarylalkyl, optionally substituted cycloalkyl, optionally substituted aryl, optionally substituted heteroaryl, carboxylic acid, ester, NR$^a$R$^b$, optionally substituted imine, hydroxyl, or oxo;

R$^2$ is hydrogen, NR$^a$R$^b$, optionally substituted imine, optionally substituted alkyl, or optionally substituted aryl; and R$^a$ and R$^b$, at each occurrence, are each independently hydrogen, optionally substituted alkyl, or optionally substituted aryl.

The thionucleobase may stabilize the benzothiazole luciferin analog against decomposition over time, in the presence of light, in the absence of light, and/or at different temperatures. The thionucleobase may stabilize the benzothiazole luciferin analog against decomposition into one or more decomposition products over time, in the presence of light, in the absence of light, and/or at different temperatures.

As such, inclusion of the thionucleobase in the composition may stabilize the benzothiazole luciferin analog against decomposition by suppressing or reducing the formation of the one or more decomposition products as compared to a composition that does not include the thionucleobase. This, in turn, provides the capability of storing or incubating the benzothiazole luciferin analog for a period of time at a particular temperature, in the presence and/or in the absence of light, without significant decomposition of the benzothiazole luciferin analog before use of the benzothiazole luciferin analog in an assay.

The present invention also relates to a method for stabilizing the benzothiazole luciferin analog. Such a method may stabilize the benzothiazole luciferin analog against decomposition and/or suppress or reduce the formation of the one or more decomposition products. The method may include contacting the benzothiazole luciferin analog with an effective amount of the thionucleobase (e.g., 0.1-500 mM) in the presence of a buffer solution. This contacting step may include forming the composition described above.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "alkyl" refers to a linear or branched hydrocarbon radical, preferably having 1 to 30 carbon atoms, 1 to 10 carbon atoms, 1 to 6 carbon atoms or 1 to 4 carbon atoms. The term "$C_1$-$C_4$-alkyl" is defined to include alkyl groups having 1, 2, 3, or 4 carbons in a linear or branched arrangement. For example, "$C_1$-$C_4$-alkyl" specifically includes methyl, ethyl, n-propyl, i-propyl, n-butyl, t-butyl, and i-butyl. The term "$C_1$-$C_6$-alkyl" is defined to include alkyl groups having 1, 2, 3, 4, 5 or 6 carbons in a linear or branched arrangement. For example, "$C_1$-$C_6$-alkyl" specifically includes methyl, ethyl, n-propyl, i-propyl, n-butyl, t-butyl, i-butyl, pentyl and hexyl.

As used herein, the term "alkylene" refers to a divalent group derived from a straight or branched chain hydrocarbon. Representative examples of alkylene include, but are not limited to, —$CH_2$—, —$CH_2CH_2$—, —$CH_2CH_2CH_2$—, —$CH_2CH(CH_3)CH_2$—, and —$CH_2CH(CH_3)CH(CH_3)CH_2$—.

As used herein, the term "arylalkyl" refers to an aryl group, as defined herein, appended to the parent molecular moiety through an alkyl group, as defined herein. In some embodiments, the alkyl group may be $C_1$-$C_4$-alkyl.

As used herein, the term "heteroarylalkyl" refers to a heteroaryl group, as defined herein, appended to the parent molecular moiety through an alkyl group, as defined here. In some embodiments, the alkyl group may be $C_1$-$C_4$-alkyl.

As used herein, the term "cycloalkyl" refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl.

As used herein, the term "aryl" refers to monocyclic, bicyclic, or tricyclic aromatic radicals. Representative examples of the aryl groups include, but are not limited to, phenyl, dihydroindenyl, indenyl, naphthyl, dihydronaphthalenyl, and tetrahydronaphthalenyl. Aryl groups of the present invention are optionally substituted by one or more suitable substituents, preferably 1 to 5 suitable substituents, as defined herein.

As used herein, the term "carboxylic acid" refers to COOH.

As used herein, the term "effective amount" refers to an amount of a thionucleobase compound of formula (I), as described herein, for periods of time necessary, to achieve the desired stabilization of a luciferin analog, as described herein, against decomposition into one or more decomposition products or degradants.

As used herein, the term "ester" refers to $CO_2R^c$, wherein $R^c$ is alkyl or aryl.

As used herein, the term "heteroaryl" refers to a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl includes a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinazolinyl, quinolinyl, thiazolo[5,4-b]pyridin-2-yl, thiazolo[5,4-d]pyrimidin-2-yl, and 5,6,7,8-tetrahydroquinolin-5-yl. Heteroaryl groups of the present invention may be unsubstituted or substituted by one or more suitable substituents, preferably 1 to 5 suitable substituents, as defined herein.

As used herein, the term "heterocycle" or "heterocyclyl" refers to a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of oxygen, nitrogen, phosphorus and sulfur. The three- or four-membered ring contains zero or one double bond, and one heteroatom selected from the group consisting of oxygen, nitrogen, phosphorus and sulfur. The five-membered ring contains zero or one double bond and one, two or three heteroatoms selected from the group consisting of oxygen, nitrogen, phosphorus and sulfur. The six-membered ring contains zero, one or two double bonds and one, two, or three heteroatoms selected from the group consisting of oxygen, nitrogen, phosphorus and sulfur. The seven- and eight-membered rings contains zero, one, two, or three double bonds and one, two, or three heteroatoms selected from the group consisting of oxygen, nitrogen, phosphorus and sulfur. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, phosphinane, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydropyrimidinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, and 2,5-dioxo-pyrrolidinyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, 9-phosphabicyclo[3.3.1]nonane, 8-phosphabicyclo[3.2.1]octane, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), oxa-adamantane (2-oxatricyclo[3.3.1.1$^{3,7}$]decane), and 2,4,6-trioxa-8-phosphatricyclo[3.3.1.13,7]decane. Heterocyclic groups of the present invention may be unsubstituted or substituted by one or more suitable substituents, preferably 1 to 3 suitable substituents, as defined above. Heterocyclic groups of the present invention may contain one or more oxo groups (=O) or thioxo (=S) groups attached to the ring.

As used herein, the term "imine" refers to —N=CR$^d$, wherein R$^d$ is alkyl, aryl, heteroaryl, or cycloalkyl, as defined herein. R$^d$ may be unsubstituted or substituted by one or more suitable substituents, as defined herein.

As used herein, the term "hydroxy" refers to an —OH group.

As used herein, the term "oxo" refers to a double bonded oxygen (=O) radical wherein the bond partner is a carbon atom. Such a radical can also be thought as a carbonyl group.

As used herein, the term "suitable substituent" is intended to mean a chemically acceptable functional group e.g., a moiety that does not negate the activity of the inventive compounds. Illustrative examples of suitable substituents include, but are not limited to, halo groups, perfluoroalkyl groups, perfluoroalkoxy groups, alkyl groups, alkenyl groups, alkynyl groups, hydroxy groups, halo groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl—and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. The substituents can be substituted by additional substituents.

If substituents are described as being "independently selected" from a group, each substituent is selected independent of the other. Each substituent, therefore, may be identical to or different from the other substituent(s).

As used herein, the term "light" may refer to visible light, white light (which may be a combination of the three primary colors red light, blue light, and yellow light), violet light, blue light, blue-green light, green light, yellow-green light, yellow light, orange light, red light, or near ultraviolet light, or any combination thereof. The term "light" may refer to light from a region of the electromagnetic spectrum, for example, but not limited to, the visible light region. The term "light" may also refer to light having a wavelength of about 380 nm to about 780 nm, or about 400 nm to about 700 nm. The term "light" may further refer to light from a fluorescent light bulb, a light-emitting diode (LED) bulb, an incandescent light bulb, or any combination thereof. In some embodiments, dark may be an absence of light.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOSITION

The present invention is directed to a composition comprising a benzothiazole luciferin analog, a thionucleobase, and optionally a liquid medium. The composition may stabilize the benzothiazole luciferin analog against decomposition. The composition may stabilize the benzothiazole luciferin analog against decomposition as compared to a composition that does not contain the thionucleobase. The thionucleobase may reduce or suppress the formation of one or more decomposition products from the benzothiazole luciferin analog. For example, and as described below in more detail, the thionucleobase may stabilize the benzothiazole luciferin analog against decomposition to one or more decomposition products such as a benzothiazole dehydroluciferin.

The present composition can be in a dry form, which is essentially free of any liquid or moisture. Alternatively, the composition can also be in a liquid form, which includes a liquid medium.

The composition may stabilize the benzothiazole luciferin analog against decomposition in the absence of light (i.e., in the dark). The composition may increase the half-life of the benzothiazole luciferin analog in the absence of light as compared to a composition that does not contain the thionucleobase.

The composition may stabilize the benzothiazole luciferin analog against decomposition in the presence of light. The composition may increase the half-life of the benzothiazole luciferin analog in the presence of light as compared to a composition that does not contain the thionucleobase. The composition may increase the half-life of the benzothiazole luciferin analog in the presence of light about 1.1-fold, 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold, 3.5-fold, 3.6-fold, 3.7-fold, 3.8-fold, 3.9-fold, 4.0-fold, 4.1-fold, 4.2-fold, 4.3-fold, 4.4-fold, 4.5-fold, 4.6-fold, 4.7-fold, 4.8-fold, 4.9-fold, or 5.0-fold as compared to the composition that does not contain the thionucleobase.

The composition may stabilize the benzothiazole luciferin analog against decomposition at temperatures from about −120° C. to about 80° C., about −110° C. to about 80° C., about −100° C. to about 80° C., about −90° C. to about 80° C., about −85° C. to about 80° C., about −80° C. to about 80° C., about −75° C. to about 80° C., about −70° C. to about 80° C., about −65° C. to about 80° C., about −60° C. to about 80° C., about −55° C. to about 80° C., about −50° C. to about 80° C., about −45° C. to about 80° C., about −40° C. to about 80° C., about −35° C. to about 80° C., about −30° C. to about 80° C., about −25° C. to about 80° C., about −20° C. to about 80° C., about −15° C. to about 80° C., about −10° C. to about 80° C., about −5° C. to about 80° C., about 0° C. to about 80° C., about −120° C. to about 75° C., about −120° C. to about 70° C., about −120° C. to about 65° C., about −120° C. to about 60° C., about −120° C. to about 55° C., about −120° C. to about 50° C., about −120° C. to about 45° C., about −120° C. to about 40° C., about −120° C. to about 35° C., about −120° C. to about 30° C., about −120° C. to about 25° C., about −120° C. to about 20° C., about −100° C. to about 70° C., about −80° C. to about 60° C., about −80° C. to about 55° C., about −80° C. to about 50° C., about −80° C. to about 45° C., about −80° C. to about 40° C., about −80° C. to about 35° C., about −80° C. to about 30° C., about −80° C. to about 25° C., about −20° C. to about 60° C., about −20° C. to about 55° C., about −20 to about 50° C., about −20° C. to about 45° C., about −20° C. to about 40° C., about −20° C. to about 35° C., about −20° C. to about 30° C., or about −20° C. to about 25° C.

The composition may stabilize the benzothiazole luciferin analog against decomposition at about −120° C., −115° C., −110° C., −105° C., −100° C., −95° C., −90° C., −89° C., −88° C., −87° C., −86° C., −85° C., −84° C., −83° C., −82° C., −81° C., −80° C., −79° C., −78° C., −77° C., −76° C., −75° C., −74° C., −73° C., −72° C., −71° C., −70° C., −69° C., −68° C., −67° C., −66° C., −65° C., −64° C., −63° C., −62° C., −61° C., −60° C., −59° C., −58° C., −57° C., −56° C., −55° C., −54° C., −53° C., −52° C., −51° C., −50° C., −49° C., −48° C., −47° C., −46° C., −45° C., −44° C., −43° C., −42° C., −41° C., −40° C., −39° C., −38° C., −37° C., −36° C., −35° C., −34° C., −33° C., −32° C., −31° C., −30° C., −29° C., −28° C., −27° C., −26° C., −25° C., −24° C., −23° C., −22° C., −21° C., −20° C., −19° C., −18° C., −17° C., −16° C., −15° C., −14° C., −13° C., −12° C., −11° C., −10° C., −9° C., −8° C., −7° C., −6° C., −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 75° C., or 80° C. The composition may stabilize the benzothiazole luciferin analog against decomposition at about −80° C., about −20° C., about 4° C., or about 20° C.

The composition may stabilize the benzothiazole luciferin analog against decomposition for at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 35 days, 40 days, 45 days, 50 days, 55 days, 60 days, 65 days, 70 days, 75 days, 80 days, 85 days, 90 days, 100 days, 110 days, 120 days, 130 days, 140 days, 150 days, 160 days, 170 days, 180 days, 190 days, 200 days, 210 days, 220 days, 230 days, 240 days, 250 days, 260 days, 270 days, 280 days, 290 days, 300 days, 310 days, 320 days, 330 days, 340 days, 350 days, 360 days, 1 year, 2 years, 3 years, 4 years, or 5 years.

The composition may increase the half-life of the benzothiazole luciferin analog by at least about 1.25-fold, 1.5-fold, 1.75-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, or 25-fold as compared to the composition that does not include the thionucleobase.

a. Benzothiazole Luciferin Analog

Benzothiazole luciferin analogs according to the invention include those described in WO2006/130551, WO2014/159044, US2007/0015790, US2014/0304842, US2018/0155762, U.S. Pat. Nos. 5,098,828, 7,692,022, or U.S. Pat. No. 7,910,087, which are incorporated by reference herein in their entireties. For example, a benzothiazole luciferin analog as disclosed herein includes a compound of formula (II'), or a salt thereof.

In some embodiments, $W^1$ and $W^2$ are hydrogen. In some embodiments, the benzothiazole luciferin analog is a compound of formula (II'), wherein $W^1$ is hydrogen and $W^2$ is $C_1$-$C_4$alkyl or arylalkyl. For example, $W^2$ may be methyl, ethyl, propyl, isopropyl, n-butyl, i-butyl, t-butyl, or benzyl.

In some embodiments, the benzothiazole luciferin analog is a compound of formula (II'), wherein $W^1$ and $W^2$ are each independently $C_1$-$C_4$alkyl. For example, $W^1$ and $W^2$ may be each independently methyl, ethyl, propyl, isopropyl, n-butyl, i-butyl, t-butyl, or benzyl. In some embodiments, $W^1$ and $W^2$ are both methyl, ethyl, propyl, isopropyl, n-butyl, i-butyl, t-butyl, or benzyl.

In some embodiments, the benzothiazole luciferin analog is a compound of formula (II'), wherein $W^1$ and $W^2$ together with the carbon to which they are attached form a $C_3$-$C_8$cycloalkyl, optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl). For example, $W^1$ and $W^2$ together with the carbon to which they are attached may form

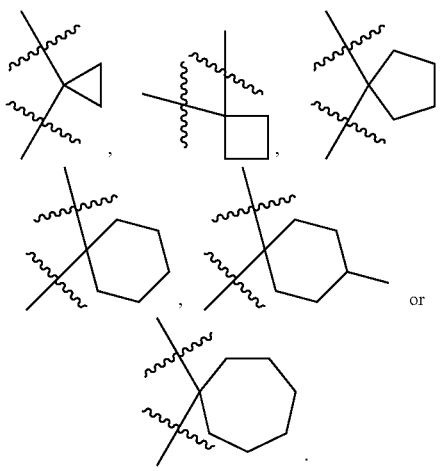

In some embodiments, the benzothiazole luciferin analog is a compound of formula (II'), wherein $W^1$ and $W^2$ together with the carbon to which they are attached form a 4- to 8-membered heterocycle, optionally substituted with a 1-4 substituents independently selected from the group consisting of $C_1$-$C_4$alkyl, $C_1$-$C_4$haloalkyl, halo, hydroxy, oxo, and —O($C_1$-$C_4$alkyl). For example, $W^1$ and $W^2$ together with the carbon to which they are attached may form

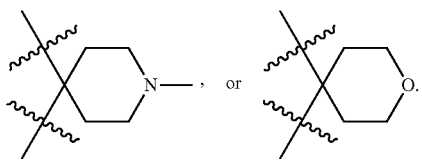

In some embodiments, the benzothiazole luciferin analog is a compound of formula (II), or salt thereof.

In some embodiments, the benzothiazole luciferin analog may be a benzothiazole luciferin, for example D-luciferin. In other embodiments, the benzothiazole luciferin analog may be a benzothiazole luciferin such as an aminoluciferin, for example, the compound of formula (II') or formula (II) where $R^{1'}$, $R^{2'}$, $R^{3'}$, and $R^{5'}$ are each H and $R^{4'}$ is $NH_2$. A benzothiazole luciferin is a substrate for a luciferase enzyme.

In other embodiments, the benzothiazole luciferin analog may be a benzothiazole pro-luciferin. As used herein, a benzothiazole pro-luciferin does not support luminescence directly when combined with a luciferase, but can be converted into a benzothiazole luciferin by biotransformation, e.g., with a second enzyme. Benzothiazole pro-luciferins include, for example, a compound of formula (II') or formula (II) wherein $R^{4'}$ is —$OG^1$, —$NHG^1$, or —$N(C_1$-$C_4$alkyl)$G^1$; and $G^1$ comprises an enzyme substrate, wherein biotransformation of the enzyme substrate by an enzyme converts $G^1$ to H. Another exemplary benzothiazole proluciferin includes a compound of formula (II') or formula (II), wherein $R^{1'}$ is —$C_2$alkylene-OH, $R^{2'}$ is H, $R^{3'}$ is H, $R^{5'}$ is H, and $R^{4'}$ is —$OCH_3$.

$G^1$ comprises an enzyme substrate, wherein biotransformation of the enzyme substrate by an enzyme converts $G^1$ to H. In some embodiments, $G^1$ is $G^2$-$L^1$-; $G^2$ is the enzyme substrate and $L^1$ is a linker connecting $G^2$ to the remainder of the compound of formula (II') or formula (II) (i.e., the parent molecular moiety). $G^2$ is a group removable by an enzyme.

In some embodiments, $L^1$ is a bond or a divalent group composed of an arrangement of atoms stable under neutral ambient conditions, the atoms being selected from carbon, hydrogen, nitrogen, oxygen, sulfur, phosphorus, and silicon. The divalent group may include single (e.g., $CH_2$—$CH_2$, $CH_2$—O), double (e.g., C=O), or triple bonds (e.g., C≡C), and may contain or include ring structures (e.g., a cycloalkyl). In some embodiments, the divalent group is an arrangement of one or more of —$C_{1-10}$alkylene-, —$C_{2-10}$alkylene-O—, $C_{3-8}$cycloalkylene, —C(O)—, —O—, —S—, —S(O)—, —S(O)$_2$—, —NH—, —N($C_{1-4}$alkyl)-, —N(COC$_{1-4}$alkyl)-, an amino acid moiety, a protected amino acid moiety, and phenylene, wherein the $C_{3-8}$cycloalkylene and phenylene are optionally independently substituted with 1-4 substituents independently selected from the group consisting of $C_{1-4}$alkyl, $C_{1-4}$haloalkyl, $C_{1-4}$alkoxy, halo, cyano, or hydroxy. In some embodiments, $L^1$ is $C_1$-$C_{10}$alkylene (e.g., $C_2$-$C_3$alkylene).

Linker $L^1$ may be a linker between a benzothiazole luciferin and an enzyme substrate as disclosed in WO2006/130551, WO2014/159044, US2007/0015790, or US2014/0304842, which are incorporated herein by reference in their entireties. For example, $L^1$ may be a traceless linker such as trimethyl lock, quinone methide, dipeptidyl, para-amino benzyloxycarbonyl, or alkylenediaminocarbonyl linkers as shown in Scheme 1. Enzymatic biotransformation of $G^2$ results in cleavage of the bond to the heteroatom to which $G^2$ is attached to release the linker that may spontaneously self immolate to release a benzothiazole luciferin analog. Some traceless linkers (e.g., alkylene linkers) may be spontaneously eliminated by β-elimination, as described in WO2006/130551.

Scheme 1

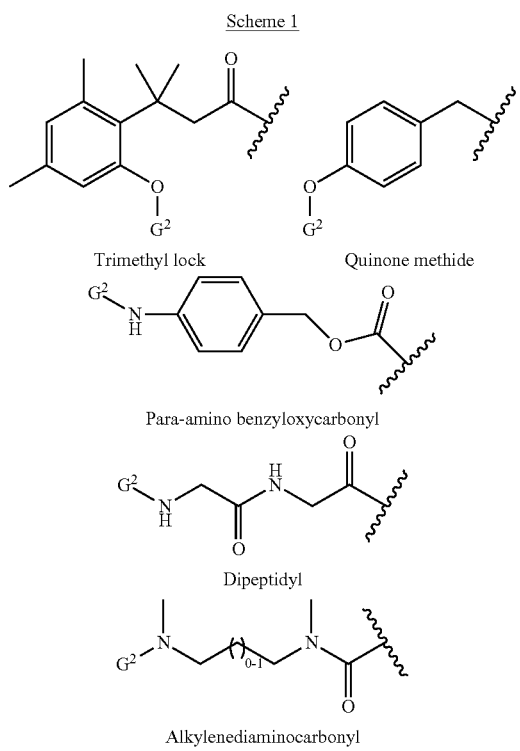

Representative examples of an enzyme substrate $G^2$ include a substrate for a protease, a cytochrome (CYP) P450 reductase, a monoamineoxidase (MAO), a flavin monooxygenase (FMO), glutathione S transferase (GST), a dealkylase (e.g., demethylase), a deacetylase, a deformylase, a sulfatase, a phosphatase (e.g., alkaline phosphatase (AP)), a beta-lactamase, and alcohol dehydrogenase, as described in WO2006/130551 or US2007/0015790, which are incorporated herein by reference in their entireties.

Representative protease substrates include, but are not limited to, the peptides Z-DEVD-, Z-LETD-, GP-, Suc-LLVY-, Z-LRR-, Z-nLPnLD-, Z-QEVY-, VP-, Z-VDVAD-, Z-VEID-, Z-ATAD-, Z-IEPD-, Z-IETD-, Z-TSAVLQ-, and Z-VNSTLQ- as described by Cosby et al. in Cell Notes (2007) 18, pp. 9-11, which is incorporated herein by reference in its entirety. In the case of these protease substrates, $L^1$ is a bond, as the enzyme substrate is directly attached to the —X— and is cleaved directly.

Representative examples of $G^1$ with traceless linkers are shown in Scheme 2.

Scheme 2

[Scheme 2 depicts multiple chemical structures of protecting/linker groups including phosphate, sulfate, methoxybenzyl, acetoxybenzyl, phosphate-benzyl, trimethyl-benzoquinone amide, thiophenyl, aminoalkyl, cephalosporin, methoxybenzyl ether with phenyl-dimethylamino substituent, and nitro-trifluoromethylphenyl groups.]

Certain embodiments of a benzothiazole luciferin analog include the compound of formula (II') or formula (II) wherein $$\overset{\xi}{\underset{\xi}{\bigcirc}}_{A}$$

is (a)

$$\begin{array}{c} R^{5'} \\ R^{4'} \\ \\ R^{3'} \\ R^{2'} \end{array} ;$$

$R^{1'}$, $R^{2'}$, $R^{3'}$, and $R^{5'}$ are H; $R^{4'}$ is —XG or —XG$^1$; G, at each occurrence is independently H, $C_1$-$C_{12}$alkyl, or two G together with the nitrogen atom to which they are attached form a 4- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl); and X and G$^1$ are as defined herein.

In other embodiments, $$\overset{\xi}{\underset{\xi}{\bigcirc}}_{A}$$

is (a)

$$\begin{array}{c} R^{5'} \\ R^{4'} \\ \\ R^{3'} \\ R^{2'} \end{array} ;$$

$R^{4'}$ is —XG; X is as defined herein; and at least one G together with one of $R^{3'}$ or $R^{5'}$ forms a 5- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl). In some embodiments, one G together with $R^{3'}$ forms a 5- to 8-membered monocyclic heterocyclic ring optionally substituted as described herein. In some embodiments, X is —NH— or —N($C_1$-$C_{12}$alkyl)- (e.g., —N($CH_3$)—) and G together with $R^{3'}$ forms a 5- to 8-membered monocyclic heterocyclic ring optionally substituted as described herein. In some embodiments, the optionally substituted heterocyclic ring formed between G and $R^{3'}$ is selected from the group consisting of

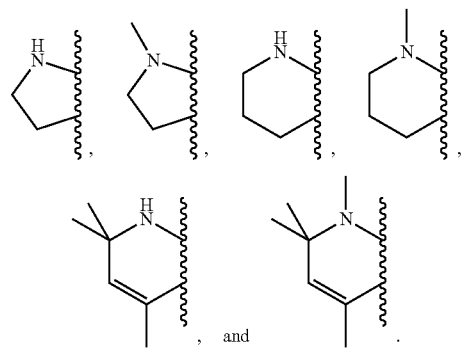

, and .

In some embodiments, the benzothiazole luciferin analog is

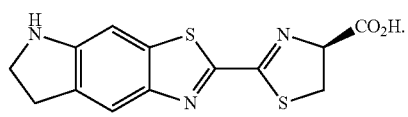 [SMILES: O=C(O)[C@H]1CSC(c2nc3cc4c(cc3s2)NCC4)=N1]

In some embodiments, one G together with $R^{5'}$ forms a 5- to 8-membered monocyclic heterocyclic ring optionally substituted as described herein. In some embodiments, X is —NH— or —N($C_1$-$C_{12}$alkyl)- (e.g., —N($CH_3$)—) and G together with $R^{5'}$ forms a 5- to 8-membered monocyclic heterocyclic ring optionally substituted as described herein. In some embodiments, the optionally substituted heterocyclic ring formed between G and $R^{5'}$ is selected from the group consisting of

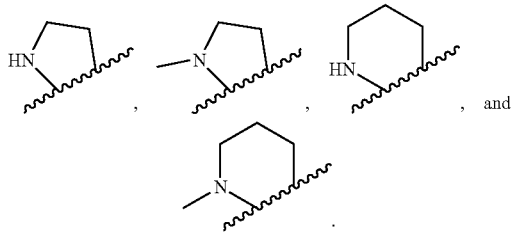

, and

In some embodiments, X is —N(G)- and each G together with one of $R^{3'}$ or $R^{5'}$ forms a 5- to 8-membered monocyclic heterocyclic ring optionally substituted as described herein (e.g.,

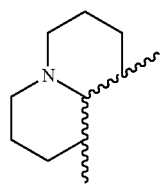

).

In some embodiments,

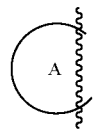

is

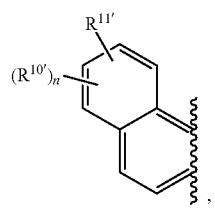

(b)

wherein $R^{1'}$, $R^{10'}$, $R^{11'}$, and n are as defined herein. In some embodiments,

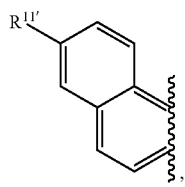

(b)

is

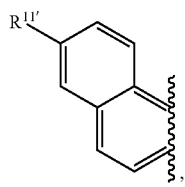

wherein $R^{1'}$ and $R^{11'}$ are as defined herein. In further embodiments, $R^{11'}$ is —OH or —$NH_2$, and $R^{1'}$ is as defined herein. In a still further embodiment according to embodiments of (b), $R^{1'}$ is H. In some embodiments, the benzothiazole luciferin analog is

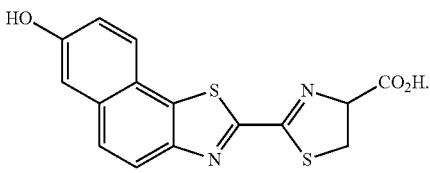 [SMILES: O=C(O)C1CSC(c2nc3ccc4cc(O)ccc4c3s2)=N1]

In other embodiments, the benzothiazole luciferin analog is

In some embodiments,

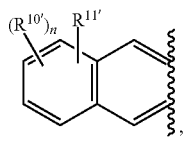

is

(c)

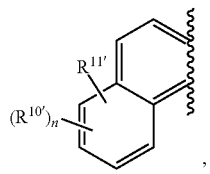

wherein $R^{1'}$, $R^{10'}$, $R^{11'}$, and n are as defined herein.

In some embodiments, (A)

is (d)

wherein, $R^{1'}$, $R^{10'}$, $R^{11'}$, and n are as defined herein.

In some embodiments, the present composition includes a liquid medium, and the benzothiazole luciferin analog may be present in the composition at about 0.5 mM to about 10 mM, about 0.75 mM to about 10 mM, about 1.0 mM to about 10 mM, about 0.5 mM to about 9 mM, about 0.5 mM to about 8 mM, about 0.5 mM to about 7 mM, about 0.5 mM to about 6 mM, about 0.5 mM to about 5 mM, about 0.5 mM to about 4 mM, about 0.5 mM to about 3 mM, or about 0.5 mM to about 2 mM. The benzothiazole luciferin analog may be present in the composition at about 0.5 mM, 0.6 mM, 0.7 mM, 0.8 mM, 0.9 mM, 1.0 mM, 1.1 mM, 1.2 mM, 1.25 mM, 1.3 mM, 1.4 mM, 1.5 mM, 1.6 mM, 1.7 mM, 1.8 mM, 1.9 mM, 2 mM, 2.5 mM, 3 mM, 3.5 mM, 4 mM, 4.5 mM, 5 mM, 5.5 mM, 6 mM, 6.5 mM, 7 mM, 7.5 mM, 8 mM, 8.5 mM, 9 mM, 9.5 mM, or 10 mM.

b. Thionucleobase

The composition may include a thionucleobase. The thionucleobase may stabilize the benzothiazole luciferin analog against decomposition into one or more decomposition products. The thionucleobase may reduce or suppress the formation of the one or more decomposition products. Such stabilization, reduction, or suppression may be in the presence of light, in the absence of light, and/or at different temperatures as described above.

The thionucleobase may be a compound of formula (I) or a tautomer thereof,

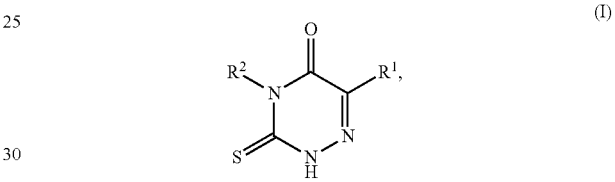

wherein $R^1$ is hydrogen, optionally substituted alkyl, optionally substituted arylalkyl, optionally substituted heteroarylalkyl, optionally substituted cycloalkyl, optionally substituted aryl, optionally substituted heteroaryl, carboxylic acid, ester, $NR^aR^b$, optionally substituted imine, hydroxyl, or oxo;

$R^2$ is hydrogen, $NR^aR^b$, optionally substituted imine, optionally substituted alkyl, or optionally substituted aryl; and $R^a$ and $R^b$, at each occurrence, are each independently hydrogen, optionally substituted alkyl, or optionally substituted aryl.

In certain embodiments, $R^1$ is hydrogen, alkyl, arylalkyl, heteroarylalkyl, cycloalkyl, aryl, heteroaryl, carboxylic acid, ester, $NR^aR^b$, imine, hydroxyl, or oxo; wherein $R^a$ and $R^b$ are each independently hydrogen, alkyl, or aryl; and wherein said alkyl, aryl, heteroaryl, cycloalkyl, arylalkyl, heteroarylalkyl, and imine, at each occurrence, are independently unsubstituted or substituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, cycloalkylalkyl, heteroarylalkyl, arylalkyl, hydroxy, hydroxyalkyl, hydroxyfluoroalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In certain embodiments, $R^1$ is alkyl, arylalkyl, heteroarylalkyl, cycloalkyl, carboxylic acid, ester, or oxo; wherein said alkyl, cycloalkyl, and arylalkyl, at each occurrence, are independently unsubstituted or substituted with 1, 2, or 3 functional groups independently selected from the group consisting of halogen, nitro, hydroxy, amino, alkylamino, and —COOH.

In certain embodiments, $R^2$ is hydrogen, $NR^aR^b$, imine, alkyl, or aryl; wherein $R^a$ and $R^b$ are each independently hydrogen, alkyl, or aryl; wherein said alkyl, imine, and aryl, at each occurrence, are independently unsubstituted or substituted with 1, 2, 3, 4, 5, 6, or 7 functional groups independently selected from the group consisting of halogen, =O, =S, cyano, cyanoalkyl, cyanofluoroalkyl, nitro, fluoroalkyl, alkoxyfluoroalkyl, fluoroalkoxy, alkyl, alkenyl, alkynyl, haloalkyl, haloalkoxy, heteroalkyl, cycloalkyl, halocycloalkyl, cycloalkenyl, aryl, heteroaryl, heterocycle, cycloalkylalkyl, heteroarylalkyl, arylalkyl, hydroxy, hydroxyalkyl, hydroxyfluoroalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In certain embodiments, $R^2$ is hydrogen, $NR^aR^b$, or imine; wherein $R^a$ and $R^b$ are each independently hydrogen or alkyl; wherein said imine is unsubstituted or substituted with a functional group independently selected from the group consisting of halogen, nitro, hydroxy, amino, and alkylamino.

In certain embodiments, $R^2$ is imine; wherein imine is —N=$CR^d$; wherein $R^d$ is alkyl, aryl, heteroaryl, or cycloalkyl; wherein said imine is unsubstituted or substituted with a functional group independently selected from the group consisting of halogen, nitro, hydroxy, amino, and alkylamino.

In certain embodiments, $R^2$ is imine; wherein imine is —N=$CR^d$; wherein $R^d$ is aryl or heteroaryl; wherein said imine is unsubstituted or substituted with a functional group independently selected from the group consisting of nitro and alkylamino.

The compound of formula (I) may be ATT (6-methyl-3-thioxo-3,4-dihydro-1,2,4-triazin-5(2H)-one), which has the following structure:

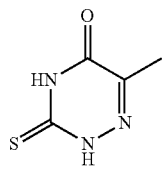

ATT may also be known as 6-Aza-2-thiothymine. ATT is commercially available, for example, from Sigma-Aldrich (catalog number 275514).

The compound of formula (I) may be ATCA (5-oxo-3-thioxo-2,3,4,5-tetrahydro-1,2,4-triazine-6-carboxylic acid), which has the following structure:

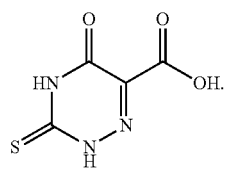 [SMILES: O=C(O)c1n[nH]c(=S)[nH]c1=O]

ATCA is commercially available, for example, from Sigma-Aldrich (catalog number S784028).

The compound of formula (I) may be 3-(4-Amino-5-oxo-3-thioxo-2,3,4,5-tetrahydro-1,2,4-triazin-6-yl)propanoic acid, which has the following structure:

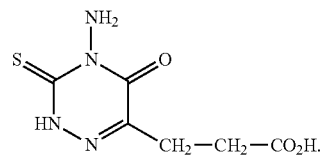 [SMILES: Nn1c(=S)[nH]nc(CCC(=O)O)c1=O]

This compound is commercially available, for example, from Sigma-Aldrich (catalog number OTV000379.

The compound of formula (I) may be tetrahydro-2-methyl-3-thioxo-1,2,4-triazine-5,6-dione, which has the following structure:

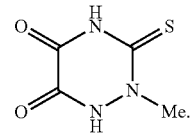

This compound may also be known as thiotriazinone and is commercially available, for example, from Sigma Aldrich (catalog number 549756).

The compound of formula (I) may be 4-((2-furylmethylene)amino)-3-mercapto-6-methyl-1,2,4-triazin-5(4H)-one, which has the following structure:

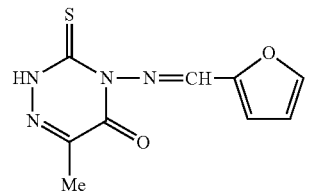

This compound is commercially available, for example, from Sigma Aldrich (catalog number L125016).

The compound of formula (I) may be 6-benzyl-3-sulfanyl-1,2,4-triazin-5-ol, which has the following structure:

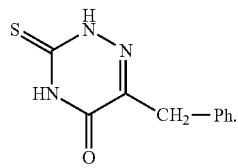 [SMILES: O=c1[nH]c(=S)[nH]nc1Cc1ccccc1]

This compound may also be known as b-ATT, benzyl-ATT, or TAK-0002.

The compound of formula (I) may be 4-amino-3-mercapto-6-methyl-1,2,4-triazin-5(4H)-one, which has the following structure:

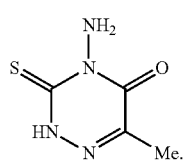

This compound is commercially available, for example, from Sigma-Aldrich (catalog number PH125903).

The compound of formula (I) may be 3-(5-oxo-3-thioxo-2,3,4,5-tetrahydro-1,2,4-triazin-6-yl)propanoic acid, which has the following structure:

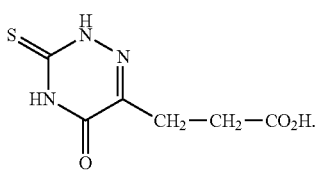 [SMILES: O=C(O)CCc1n[nH]c(=S)[nH]c1=O]

This compound is commercially available, for example, from Sigma-Aldrich (catalog number L151629).

The compound of formula (I) may be (E)-6-methyl-4-((thiophen-2-ylmethylene)amino)-3-thioxo-3,4-dihydro-1,2,4-triazin-5(2H)-one, which has the following structure:

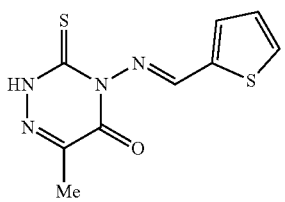

This compound is commercially available, for example, from Sigma Aldrich (catalog number L150819).

The compound of formula (I) may be (E)-6-methyl-4-((3-nitrobenzylidene)amino)-3-thioxo-3,4-dihydro-1,2,4-triazin-5(2H)-one, which has the following structure:

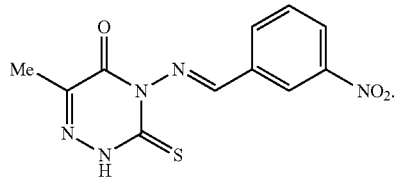 [SMILES: Cc1n[nH]c(=S)n(/N=C/c2cccc([N+](=O)[O-])c2)c1=O]

This compound is commercially available, for example, from Sigma Aldrich (catalog number L151238).

The compound of formula (I) may be (E)-4-((4-(diethylamino)benzylidene)amino)-6-methyl-3-thioxo-3,4-dihydro-1,2,4-triazin-5(2H)-one, which has the following structure:

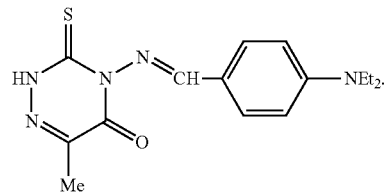

This compound is commercially available, for example, from Sigma Aldrich (catalog number L151211).

The compound of formula (I) may be ATCA ethyl ester, which has the following structure:

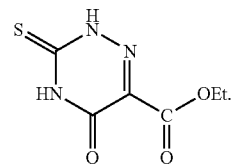 [SMILES: CCOC(=O)c1n[nH]c(=S)[nH]c1=O]

This compound is commercially available, for example, from Sigma Aldrich (catalog number PH008592).

The compound of formula (I) may be TAK-0021, which has the following structure:

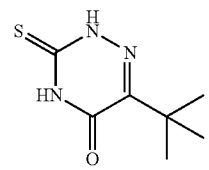

The compound of formula (I) may be TAK-0020, which has the following structure:

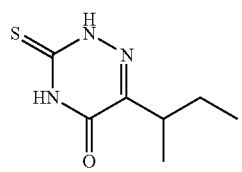

The compound of formula (I) may be TAK-0018, which has the following structure:

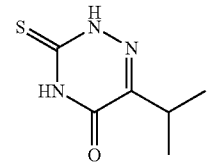

The compound of formula (I) may be TAK-0009, which has the following structure:

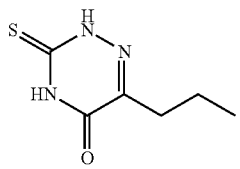

The compound of formula (I) may be TAK-0014, which has the following structure:

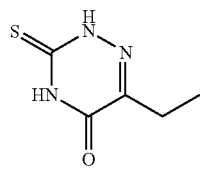

The compound of formula (I) may be TAK-0007, which has the following structure:

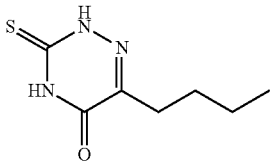

The compound of formula (I) may be TAK-0008, which has the following structure:

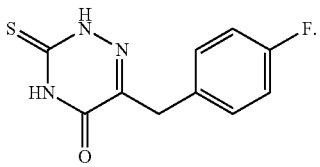 [SMILES: O=c1[nH]c(=S)[nH]nc1Cc1ccc(F)cc1]

The compound of formula (I) may be TAK-0003, which has the following structure:

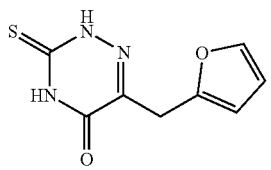

The compound of formula (I) may be TAK-0004, which has the following structure:

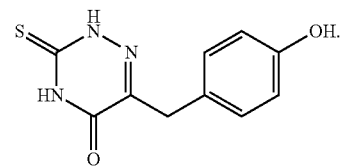 [SMILES: O=c1[nH]c(=S)[nH]nc1Cc1ccc(O)cc1]

The compound of formula (I) may be 3-thioxo-6-(trifluoromethyl)-3,4-dihydro-1,2,4-triazin-5(2H)-one, which has the following structure:

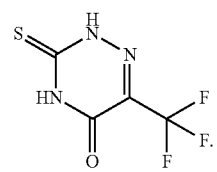 [SMILES: O=c1[nH]c(=S)[nH]nc1C(F)(F)F]

The compound of formula (I) may be 6-cyclopropyl-3-thioxo-3,4-dihydro-1,2,4-triazin-5(2H)-one, which has the following structure:

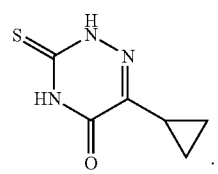 [SMILES: O=c1[nH]c(=S)[nH]nc1C1CC1]

The compound of formula (I) may be 6-(hydroxymethyl)-3-thioxo-3,4-dihydro-1,2,4-triazin-5(2H)-one, which has the following structure:

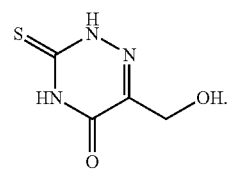

TAK-0014, TAK-0002, TAK-0021, TAK-0020, TAK-0018, TAK-0009, TAK-0007, TAK-0008, TAK-0003, TAK-0004, 3-thioxo-6-(trifluoromethyl)-3,4-dihydro-1,2,4-triazin-5(2H)-one, 6-cyclopropyl-3-thioxo-3,4-dihydro-1,2,4-triazin-5(2H)-one, and 6-(hydroxymethyl)-3-thioxo-3,4-dihydro-1,2,4-triazin-5(2H)-one were synthesized as described in S. J. Liu et al., ARKIVOC (2009) 333-348 and S. J. Liu et al., Letters in Drug Design and Discovery (2010) 7:5-8, the entire contents of both of which are herein incorporated by reference.

The thionucleobase may be present in the composition at an amount effective to stabilize the benzothiazole luciferin analog against decomposition. In some embodiments, the present composition includes a liquid medium, and the effective amount of the thionucleobase in the composition to stabilize the luciferin analog against decomposition may be about 0.1 mM to about 500 mM, about 0.5 mM to about 500 mM, about 1 mM to about 500 mM, about 5 mM to about 500 mM, about 10 mM to about 500 mM, about 15 mM to about 500 mM, about 20 mM to about 500 mM, about 30 mM to about 500 mM, about 50 mM to about 500 nM, about 70 mM to about 500 mM, about 90 mM to about 500 mM, about 110 mM to about 500 mM, about 130 mM to about 500 mM, about 150 mM to about 500 mM, about 170 mM to about 500 mM, about 190 mM to about 500 mM, about 210 mM to about 500 mM, about 0.1 mM to about 475 mM, about 0.1 mM to about 450 mM, about 0.1 mM to about 425 mM, about 0.1 mM to about 400 mM, about 0.1 mM to about 375 mM, about 0.1 mM to about 350 mM, about 0.1 mM to about 325 mM, about 0.1 mM to about 300 mM, about 0.1 mM to about 275 mM, about 0.5 mM to about 450 mM, about 1 mM to about 400 mM, about 2 mM to about 350 mM, about 3 mM to about 300 mM, about 4 mM to about 300 mM, about 5 mM to about 250 mM, about 5 mM to about 200 mM, about 5 mM to about 100 mM, about 5 mM to about 50 mM, or about 5 mM to about 25 mM.

The effective amount of the thionucleobase in the composition to stabilize the benzothiazole luciferin analog against decomposition may be about 0.1 mM, 0.2 mM, 0.3 mM, 0.4 mM, 0.5 mM, 0.6 mM, 0.7 mM, 0.8 mM, 0.9 mM, 1.0 mM, 1.5 mM, 2.0 mM, 2.5 mM, 3.0 mM, 3.5 mM, 4.0 mM, 4.5 mM, 5.0 mM, 5.5 mM, 6.0 mM, 6.5 mM, 7.0 mM, 7.5 mM, 8.0 mM, 8.5 mM, 9.0 mM, 9.5 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM, 35 mM, 36 mM, 37 mM, 38 mM, 39 mM, 40 mM, 41 mM, 42 mM, 43 mM, 44 mM, 45 mM, 46 mM, 47 mM, 48 mM, 49 mM, 50 mM, 51 mM, 52 mM, 53 mM, 54 mM, 55 mM, 56 mM, 57 mM, 58 mM, 59 mM, 60 mM, 61 mM, 62 mM, 63 mM, 64 mM, 65 mM, 66 mM, 67 mM, 68 mM, 69 mM, 70 mM, 71 mM, 72 mM, 73 mM, 74 mM, 75 mM, 76 mM, 77 mM, 78 mM, 79 mM, 80 mM, 81 mM, 82 mM, 83 mM, 84 mM, 85 mM, 86 mM, 87 mM, 88 mM, 89 mM, 90 mM, 91 mM, 92 mM, 93 mM, 94 mM, 95 mM, 96 mM, 97 mM, 98 mM, 99 mM, 100 mM, 105 mM, 110 mM, 115 mM, 120 mM, 125 mM, 130 mM, 135 mM, 140 mM, 145 mM, 150 mM, 155 mM, 160 mM, 165 mM, 170 mM, 175 mM, 180 mM, 185 mM, 190 mM, 195 mM, 200 mM, 205 mM, 210 mM, 215 mM, 220 mM, 225 mM, 230 mM, 235 mM, 240 mM, 245 mM, 250 mM, 255 mM, 260 mM, 265 mM, 270 mM, 275 mM, 280 mM, 285 mM, 290 mM, 295 mM, 300 mM, 305 mM, 310 mM, 315 mM, 320 mM, 325 mM, 330 mM, 335 mM, 340 mM, 345 mM, 350 mM, 355 mM, 360 mM, 365 mM, 370 mM, 375 mM, 380 mM, 385 mM, 390 mM, 395 mM, 400 mM, 405 mM, 410 mM, 415 mM, 420 mM, 425 mM, 430 mM, 435 mM, 440 mM, 445 mM, 450 mM, 455 mM, 460 mM, 465 mM, 470 mM, 475 mM, 480 mM, 485 mM, 490 mM, 495 mM, or 500 mM.

The effective amount of the thionucleobase in the composition to stabilize the benzothiazole luciferin analog against decomposition may be greater than 0.1 mM, 0.5 mM, 1 mM, 2 mM, 5 mM, or 10 mM. In certain embodiments, the present composition contains a liquid medium, and the effective amount of the thionucleobase to stabilize the benzothiazole luciferin analog against decomposition is about 1 mM to about 10 mM, including about 2 mM to about 10 mM, about 3 mM to about 10 mM, about 4 mM to about 10 mM, about 5 mM to about 10 mM, about 6 mM to about 10 mM, about 7 mM to about 10 mM, about 8 mM to about 10 mM, and about 9 mM to about 10 mM.

In some embodiments, when the thionucleobase is ATT, the effective amount of ATT to stabilize the benzothiazole luciferin analog against decomposition may be about 0.1 mM to about 500 mM, about 1 mM to about 500 mM, about 5 mM to about 500 mM, about 10 mM to about 500 mM, about 50 mM to about 500 mM, about 100 mM to about 500 mM, about 110 mM to about 500 mM, about 120 mM to about 500 mM, about 130 mM to about 500 mM, about 140 mM to about 500 mM, about 150 mM to about 500 mM, about 160 mM to about 500 mM, about 170 mM to about 500 mM, about 180 mM to about 500 mM, about 190 mM to about 500 mM, about 200 mM to about 500 mM, about 210 mM to about 500 mM, about 90 mM to about 475 mM, about 90 mM to about 450 mM, about 90 mM to about 425 mM, about 90 mM to about 400 mM, about 90 mM to about 375 mM, about 90 mM to about 350 mM, about 90 mM to about 325 mM, about 90 mM to about 300 mM, about 90 mM to about 275 mM, about 100 mM to about 450 mM, about 125 mM to about 400 mM, about 175 mM to about 350 mM, or about 200 mM to about 300 mM.

In other embodiments, when the thionucleobase is ATT, the effective amount of ATT to stabilize the benzothiazole luciferin analog against decomposition may be about 0.1 mM, 0.2 mM, 0.3 mM, 0.4 mM, 0.5 mM, 0.6 mM, 0.7 mM, 0.8 mM, 0.9 mM, 1.0 mM, 1.5 mM, 2.0 mM, 2.5 mM, 3.0 mM, 3.5 mM, 4.0 mM, 4.5 mM, 5.0 mM, 5.5 mM, 6.0 mM, 6.5 mM, 7.0 mM, 7.5 mM, 8.0 mM, 8.5 mM, 9.0 mM, 9.5 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 105 mM, 110 mM, 115 mM, 120 mM, 125 mM, 130 mM, 135 mM, 140 mM, 145 mM, 150 mM, 155 mM, 160 mM, 165 mM, 170 mM, 175 mM, 180 mM, 185 mM, 190 mM, 195 mM, 200 mM, 201 mM, 202 mM, 203 mM, 204 mM, 205 mM, 206 mM, 207 mM, 208 mM, 209 mM, 210 mM, 211 mM, 212 mM, 213 mM, 214 mM, 215 mM, 216 mM, 217 mM, 218 mM, 219 mM, 220 mM, 221 mM, 222 mM, 223 mM, 224 mM, 225 mM, 226 mM, 227 mM, 228 mM, 229 mM, 230 mM, 231 mM, 232 mM, 233 mM, 234 mM, 235 mM, 236 mM, 237 mM, 238 mM, 239 mM, 240 mM, 241 mM, 242 mM, 243 mM, 244 mM, 245 mM, 246 mM, 247 mM, 248 mM, 249 mM, 250 mM, 251 mM, 252 mM, 253 mM, 245 mM, 255 mM, 256 mM, 257 mM, 258 mM, 259 mM, 260 mM, 261 mM, 262 mM, 263 mM, 264 mM, 265 mM, 266 mM, 267 mM, 268 mM, 269 mM, 270 mM, 271 mM, 272 mM, 273 mM, 274 mM, 275 mM, 276 mM, 277 mM, 278 mM, 279 mM, 280 mM, 281 mM, 282 mM, 283 mM, 284 mM, 285 mM, 286 mM, 287 mM, 288 mM, 289 mM, 290 mM, 291 mM, 292 mM, 293 mM, 294 mM, 295 mM, 296 mM, 297 mM, 298 mM, 299 mM, 300 mM, 305 mM, 310 mM, 315 mM, 320 mM, 325 mM, 330 mM, 335 mM, 340 mM, 345 mM, 350 mM, 355 mM, 360 mM, 365 mM, 370 mM, 375 mM, 380 mM, 385 mM, 390 mM, 395 mM, 400 mM, 405 mM, 410 mM, 415 mM, 420 mM, 425 mM, 430 mM, 435 mM, 440 mM, 445 mM, 450 mM, 455 mM, 460 mM, 465 mM, 470 mM, 475 mM, 480 mM, 485 mM, 490 mM, 495 mM, or 500 mM.

In certain embodiments, the present composition contains a benzothiazole luciferin analog, ATT, and a liquid medium, and the effective amount of ATT to stabilize the benzothiazole luciferin analog against decomposition is about 1 mM to about 10 mM, including about 2 mM to about 10 mM, about 3 mM to about 10 mM, about 4 mM to about 10 mM, about 5 mM to about 10 mM, about 6 mM to about 10 mM, about 7 mM to about 10 mM, about 8 mM to about 10 mM, and about 9 mM to about 10 mM. In other embodiment, the present composition contains a benzothiazole luciferin analog, ATT, and a liquid medium, and the effective amount of ATT to stabilize the benzothiazole luciferin analog against decomposition may be greater 10 mM, greater than about 25 mM, greater than about 50 mM, or greater than about 100 mM.

c. Dry Form Composition

The present composition can be in a dry form, which does not contain any liquid medium. In a dry composition, the benzothiazole luciferin analog and the thionucleobase may be mixed to form a solid mixture. For example, the benzothiazole luciferin analog and the thionucleobase may form a homogenous solid mixture, in which the two compounds are uniformly dispersed.

In some embodiments, the benzothiazole luciferin analog in the dry composition is a salt, which is soluble in water. The dry form compositions of these benzothiazole luciferin analogs, and the thionucleobase disclosed herein, may improve the stability of these benzothiazole luciferin analogs. In general, luciferins in salt forms have a tendency to absorb $H_2O$ during storage. Pro-luciferins and other luciferin analogs, such as the benzothiazole luciferin analogs disclosed herein, usually stored in freezers, may trap moisture during repeated use. In a moist environment, these compounds can degrade into the corresponding dehydrocompounds, which may affect the luminescent performance. As disclosed herein, inclusion of a thionucleobase with such compounds in a mixture may improve the shelf life of such compounds by slowing down decomposition. In a particular embodiment, the dry composition is a solid mixture that contains a benzothiazole luciferin analog, a thionucleobase, and other necessary ingredients, for example phosphate salts and detergents in solid form. Advantageously, the dry composition may be stored in solid form to extend the shelf life of the benzothiazole luciferin analog. In some embodiments, simple reconstitution of the dry composition disclosed herein with an appropriate amount of a liquid medium (such as $H_2O$) may provide stock solution of the benzothiazole luciferin analog that is ready to use for biological applications.

The solid mixture of the benzothiazole luciferin analog and the thionucleobase may be prepared by known methods, such as lyophilization using suitable freeze-drying instruments.

d. Liquid Medium

In some embodiments, the composition can be in a liquid form, which includes a liquid medium. In general, each of the disclosed benzothiazole luciferin analog and thionucleobase is at least partially dissolved in the liquid medium, if present. In some embodiments, the composition is in a liquid form, which includes a mixture of the disclosed benzothiazole luciferin analog and thionucleobase, both dissolved in a liquid medium.

The liquid medium may include an organic solvent, an aqueous medium, or a mixture thereof. The liquid medium may be suitable as a solvent for dissolving the benzothiazole luciferin analog or the thionucleobase compound disclosed herein, or a mixture thereof. In certain embodiments, the liquid medium may be included in a biological assay system, in which the benzothiazole luciferin analog or the thionucleobase compound disclosed herein, or a mixture thereof, is used. The biological assay system includes various systems for enzymatic assays, cellular studies, and life animal studies known in the art.

In some embodiments, the liquid medium is an organic solvent that includes one or more organic substances. The organic solvent may be used to dissolve the compounds disclosed herein to form a solution. After dissolution, the compounds may be stored in the solution at a temperature for a period of time. The solution may be added to a biological assay system immediately or after storage for a period of time. The benzothiazole luciferin analog and the thionucleobase compound, dissolved in the organic solvent, may be added to the biological assay system separately or as a mixture.

The organic solvent may be alcohol, propylene glycol, dimethyl sulfoxide (DMSO), acetonitrile, glycerol, or any combination thereof. The alcohol may be ethanol.

In some embodiments, the organic solvent may be a combination of alcohol and propylene glycol. In other embodiments, the organic solvent may be a combination of ethanol and propylene glycol. In still other embodiments, the organic solvent may be a ratio of 1:1 of ethanol:propylene glycol (e.g., 50% (v/v) ethanol:50% (v/v) propylene glycol). In another embodiment, the organic solvent may be 40% (v/v) ethanol:60% (v/v) propylene glycol.

In some embodiments, the organic solvent may be a combination of alcohol and glycerol. In other embodiments, the organic solvent may be a combination of ethanol and glycerol. In still other embodiments, the organic solvent may be 85% (v/v) ethanol:15% (v/v) glycerol.

In some embodiments, the liquid medium is an aqueous medium, such as a solution or buffer in water. The aqueous solution or buffer may be used to dissolve the compounds disclosed herein. After dissolution in the aqueous medium, the compounds may be stored in the solution at a temperature for a period of time. The solution may be added to a biological assay system immediately or after storage for a period of time. The benzothiazole luciferin analog and the thionucleobase compound, dissolved in the aqueous medium, may be added to the biological assay system separately or as a mixture.

Suitable aqueous media may include various buffers at approximately pH 6-10. Non-limiting examples of suitable buffers include phosphate buffered saline (PBS), citrate, HEPES, MOPS, MES, and Tris-HCl.

In some embodiments, the composition includes a liquid medium and the thionucleobase compound is not ATT. For example, the composition may include a thionucleobase compound other than ATT, and an organic solvent selected from the group consisting of alcohol, propylene glycol, dimethyl sulfoxide (DMSO), acetonitrile, glycerol, and any combination thereof.

In some embodiments, the composition includes ATT and a liquid medium that is free of DMSO. For example, the composition may include ATT, and an organic solvent selected from the group consisting of alcohol, propylene glycol, acetonitrile, glycerol, and any combination thereof.

In some embodiments, the compounds disclosed herein are dissolved in a buffer containing a detergent. The detergent may include a cationic detergent (such as quaternary ammonium compounds), an anionic detergent (such as alkylbenzenesulfonate compounds), a nonionic detergent (such as polysorbates and various polyoxyethylene-based compounds), or mixtures thereof. In some embodiments, the detergent is a cationic detergent.

In some embodiments, the liquid medium is an aqueous medium or buffer suitable for bioluminescence determinations, such as phosphate buffers at approximately pH 6.0-8.0. Such media may additionally contain enzymes and other reagents used for bioluminescence analysis, including, for example, luciferase enzymes, reducing agents, and detergents.

e. Luciferase Enzyme

As described above, the composition may or may not include a luminogenic enzyme, a variant thereof, a mutant thereof, or any combination thereof. The luminogenic enzyme may be naturally occurring, recombinant, or mutant. The luminogenic enzyme may use the luminogenic substrate described above (including derivatives or analogs thereof) as a substrate to catalyze a reaction that produces light or that leads to the production of light.

The luminogenic enzyme may include a luciferin-utilizing luciferase. Such luciferases include, but are not limited to, luciferases found in various organisms such as beetles (e.g., *Photinus pyralis* and *Photuris pennsylvanica* (fireflies of North America), and *Pyrophorus plagiophthalamus* (the Jamaican click beetle)). In some embodiments, the suitable luciferase may include Click Beetle Green luciferase, Click Beetle Red luciferase, and Firefly luciferase. In some embodiments, the luciferase may include a recombinant luciferase, such as the Ultra-Glo™ Luciferase (Promega Corp., Madison, Wis.).

3. METHOD OF STABILIZATION

Also provided herein is a method for stabilizing the benzothiazole luciferin analog. The method may stabilize the benzothiazole luciferin analog against decomposition. The method may stabilize the benzothiazole luciferin analog against decomposition to one or more decomposition products.

The method may include contacting the benzothiazole luciferin analog with the effective amount of the thionucleobase. In some embodiments, the contacting occurs in a solid mixture of the benzothiazole luciferin analog and the thionucleobase. For example, a dry composition containing a benzothiazole luciferin analog and a thionucleobase may be prepared using known method, in which the benzothiazole luciferin analog and the thionucleobase form a solid mixture. The thionucleobase disclosed herein may improve the stability of the benzothiazole luciferin analog in a dry composition.

The method may also include contacting the benzothiazole luciferin analog with the effective amount of the thionucleobase in the presence of a liquid medium. The liquid medium may include an organic solvent, an aqueous medium, or a mixture thereof as described above. Without being limited to any theory, it is hypothesized that the pH, temperature, light, and buffer components may influence benzothiazole luciferin stability in buffer solutions. It is unexpected that thiothymine analogs as disclosed herein (such as ATT) can stabilize benzothiazole luciferins in the liquid medium, such as in a buffer or aqueous solutions.

In some embodiments, the method includes a liquid medium and the thionucleobase compound is not ATT. For example, the method may include contacting a benzothiazole luciferin analog with a thionucleobase compound other than ATT in a liquid medium that includes an organic solvent selected from the group consisting of alcohol, propylene glycol, dimethyl sulfoxide (DMSO), acetonitrile, glycerol, and any combination thereof.

In some embodiments, the method includes ATT and a liquid medium that is free of DMSO. For example, the method may include contacting a benzothiazole luciferin analog with ATT in a liquid medium that includes an organic solvent selected from the group consisting of alcohol, propylene glycol, acetonitrile, glycerol, and any combination thereof.

The temperature range under which the thiothymine compounds may improve the stability of the benzothiazole luciferin analogs includes, but is not limited to temperatures from −80° C. to 60° C., from −40° C. to 60° C., from −20° C. to 60° C., from 0° C. to 60° C., from 20° C. to 60° C., from 30° C. to 60° C., from 30° C. to 45° C., and from 30° C. to 40° C. In some embodiments, the temperature range is one suitable for bioluminescence determinations, such as from 30° C. to 40° C., or about 37° C.

Effective amounts of the thionucleobase, which stabilize the benzothiazole luciferin analog against decomposition, are described above. Accordingly, the contacting step may include forming the composition described above, thereby stabilizing the luminogenic substrate against decomposition.

4. KIT

Also provided herein is a kit that includes the composition described above. The composition may be contained within a single container.

The kit according to the present disclosure preferably includes instructions for storing the composition and/or the single container containing the composition. Instructions included in the kit of the present disclosure may be affixed to packaging material or may be included as a package insert. While instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides instructions.

The present invention has multiple aspects, illustrated by the following non-limiting examples.

5. EXAMPLES

Example 1. Thermal Stability

Figure 2A:
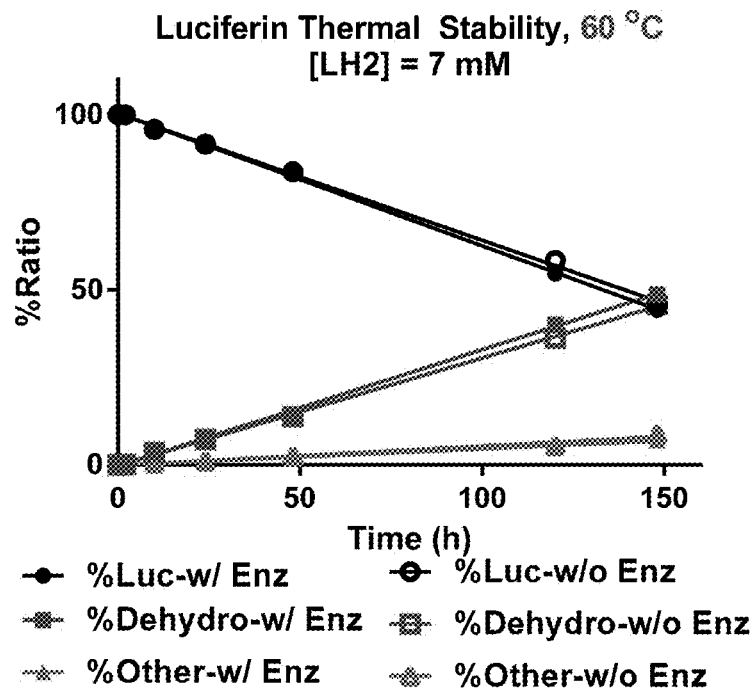
FIG. 2A shows representative thermal stability of luciferins over time.

Representative thermal stability profiling of luciferins: Luciferin stock solutions (pH=6.0, $[LH2]_{final}$=7.0 mM) containing various amounts of detergents, with or without ULTRA-GLO™ luciferase ($[enzyme]_{final}$=0.1 mg/mL; Promega) were incubated at 60° C. Aliquots (20 μL) were taken out at various time points, diluted with $H_2O$ (180 μL), and analyzed by RP-HPLC. The percentages of the components were calculated based on UV absorbance at 330 nm for 6'-OH-luciferins or 295 nm for 6'-$NH_2$-luciferins. As shown in FIG. 2A, dehydroluciferin was the major degradation product of luciferin, and the luciferase had little effect on the degradation of luciferins.

Figure 2B:
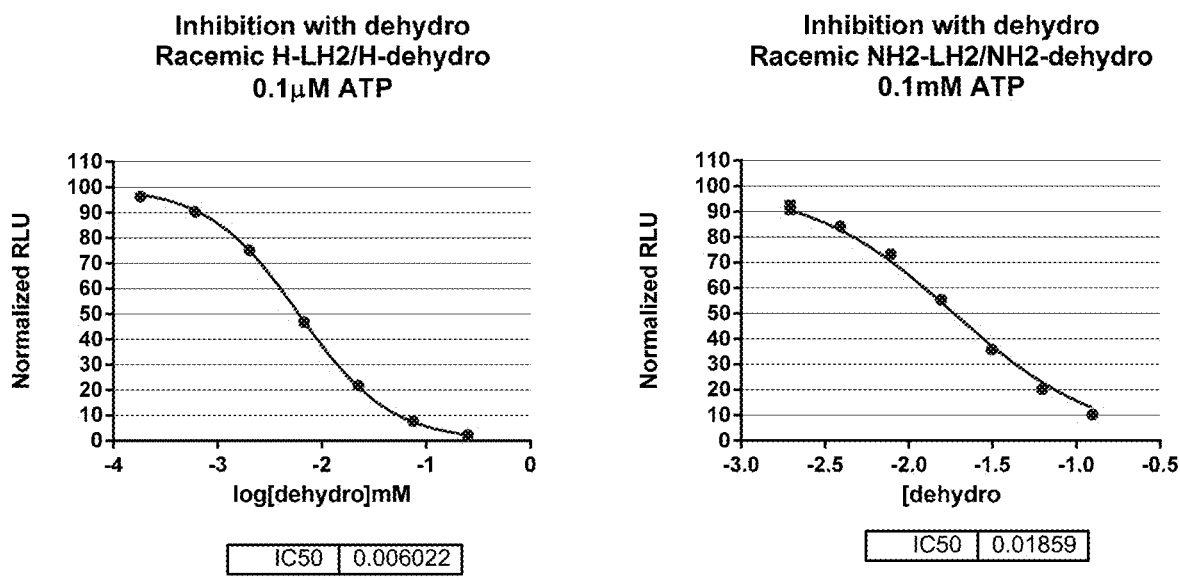
FIG. 2B shows the inhibition of luciferase activity by dehydroluciferin.

Inhibition of luciferase activity by dehydroluciferins: ULTRA-GLO™ luciferase (Promega, 0.1 mg/mL)+0.1% PRIONEX in detection reagent buffer was prepared. The solution was divided into 2 portions with 0.25 mM Racemic H-Luciferin added to one portion and 0.25 mM racemic NH2 luciferin to the other portion. H-dehydroluciferin (0.25 mM) was added to an aliquot of the racemic H-Luciferin solution, and NH2-dehydroluciferin (0.25 mM) was added to an aliquot of the racemic NH2 luciferin solution. 2× serial dilutions of each of the dehydroluciferin samples were prepared using the racemic solutions as a diluent (500 μL of dehydroluciferin solution added to 500 μL of ULTRA-GLO+racemic luciferin). 50 μL of the H-dehydroluciferin titration series was then added to 50 μL 0.2 M ATP and 50 μL of the NH2-dehydroluciferin titration was added to 50 μL of 0.2 mM ATP. The final concentration of racemic substrates was 0.125 mM and the final concentration of ATP was either 0.1 mM (for NH2-dehydroluciferin) or 0.1 μM (for H-dehydroluciferin). The samples were incubated for 1 minute, and the luminescence was measured on GLO-MAX®-Multi+ plate luminometer (n=6). As shown in FIG. 2B, dehydroluciferins were potent inhibitors of luciferases, which may account for the decreased light output after storage of luciferins stock solutions for a long period at ambient temperature.

Example 2. Stabilizing Effect

Figure 3:
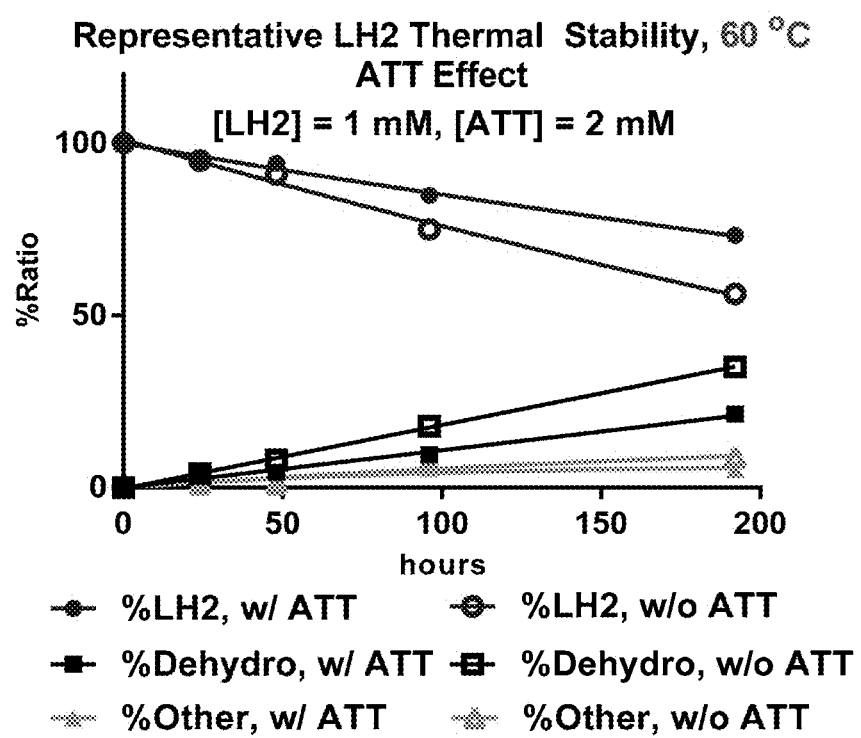
FIG. 3 shows the stability of luciferin in the presence and absence of ATT.

The effect of ATT on luciferin stability was examined by comparing the degree of luciferin decomposition in the absence or presence of ATT. Representative luciferins were reconstituted (at final concentration of 1.0 mM) in buffers containing various cationic detergents at pH 6.0, with or without ATT (Sigma, at a final concentration of 2.0 mM). The mixture was incubated at 60° C. Aliquots (20 μL) were taken out at various time points, diluted with $H_2O$ (180 μL), and analyzed by RP-HPLC. The percentages of the components were calculated based on UV absorbance at 330 nm. As demonstrated in FIG. 3, ATT reduced dehydroluciferin formation and therefore improved luciferin thermal stability by preventing its decomposition.

Figure 4A:
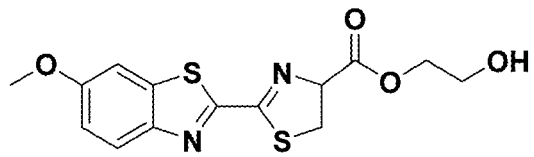
FIGS. 4A-4B show the stability of a luciferin analog, 2-hydroxyethyl ester of luciferin methyl ether (FIG. 4A) and the production of the corresponding dehydro-compound (FIG. 4B) in the presence and absence of ATT.
Figure 4A:
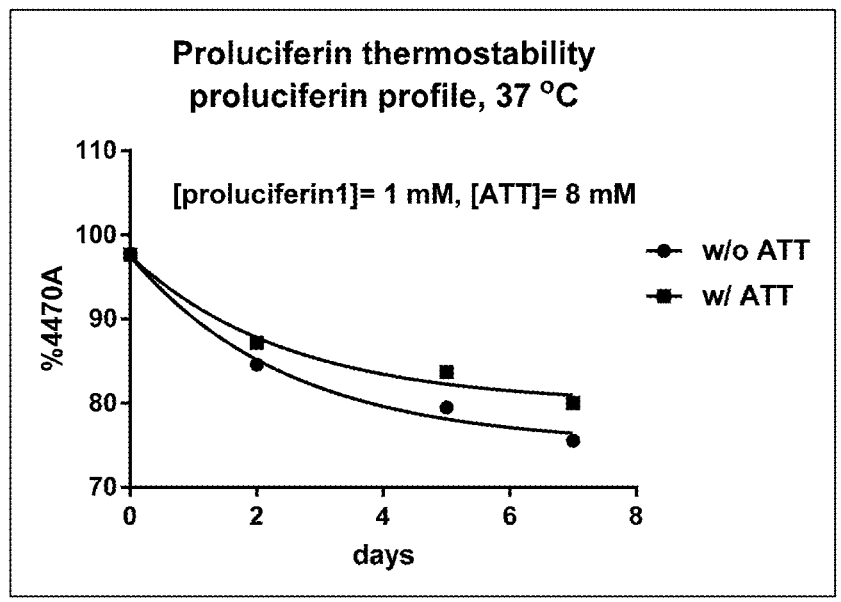
Figure 4B:
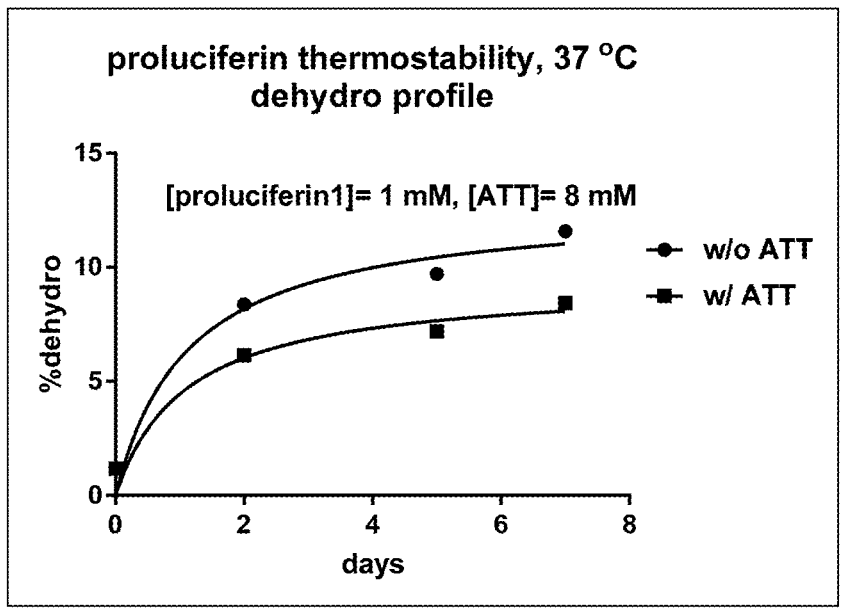

Additionally, it was found that ATT also improved the stability of pro-luciferins. The stability of 2-hydroxyethyl ester of luciferin methyl ether, which is a luminogenic, pro-luciferin substrate specific for P450 enzyme detection, was studied. A stock solution of this compound in DMSO was added to PBS buffer at pH 7.4 to reach a final concentration at 1.0 mM and 5% DMSO. The mixture was incubated at 37° C., with or without ATT (Sigma, at a final concentration of 8.0 mM). Aliquots (20 μL) were taken out at various time points, diluted with $H_2O$ (180 μL), and analyzed by RP-HPLC. The percentages of the components were calculated based on UV absorbance at 330 nm. As shown in FIG. 4, ATT slowed down the decomposition of the pro-luciferin compound and reduced the formation of the corresponding dehydroluciferin derivative.

Example 3 Bioluminescence Testing

Figure 5A:
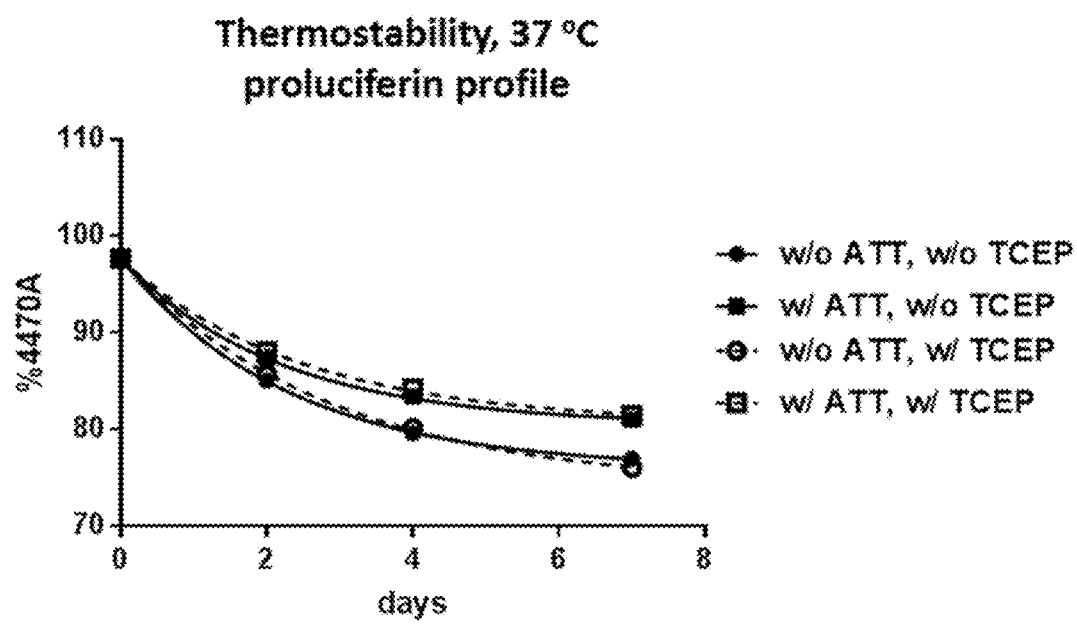
FIGS. 5A-5B show the stability of 2-hydroxyethyl ester of luciferin methyl ether (FIG. 5A) and the production of the corresponding dehydro-compound (FIG. 5B) in the presence and absence of ATT, as determined with and without the reducing agent TCEP.
Figure 5B:
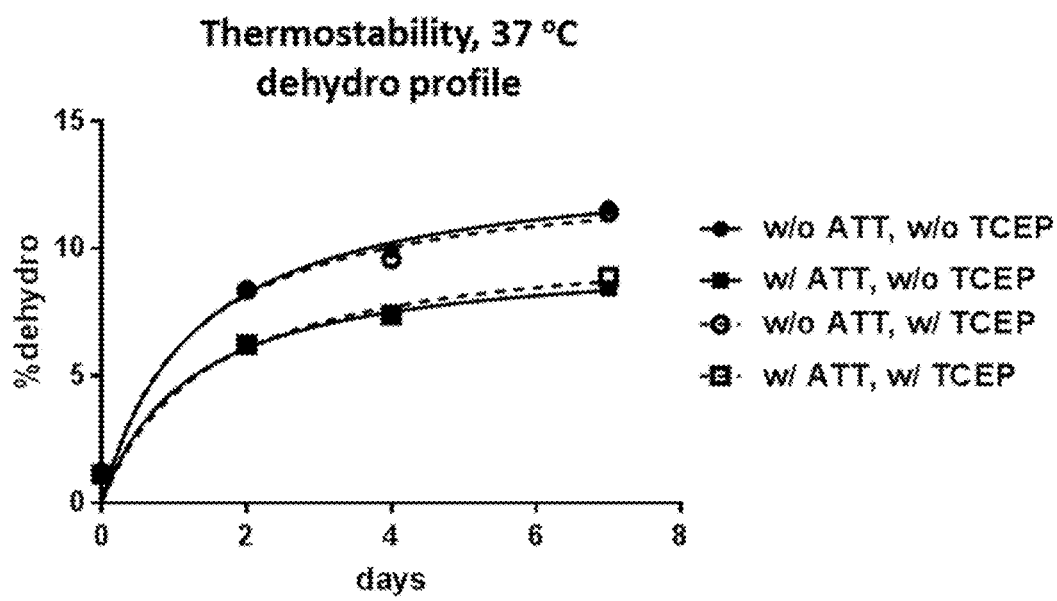

ATT was also shown to be compatible with additives that are commonly used in bioluminescence systems. A stock solution of a pro-luciferin compound, 2-hydroxyethyl ester of luciferin methyl ether, in DMSO was added to PBS buffer at pH 7.4 to reach a final concentration at 1.0 mM and 5% DMSO. The mixture was incubated at 37° C., with or without ATT (Sigma, at a final concentration of 8.0 mM), and with or without TCEP (Thermo Scientific, at a final concentration of 10 mM). Aliquots (20 μL) were taken out at various time points, diluted with $H_2O$ (180 μL), and analyzed by RP-HPLC. The percentages of the components were calculated based on UV absorbance at 330 nm. As demonstrated in FIG. 5, ATT improved the stability of the pro-luciferin compound in the presence of TCEP, a reducing agent commonly used in bioluminescence studies. Specifically, the presence of TCEP does not affect the ability of ATT to reduce the proluciferin decomposition (top panel) and the dehydro-compound production (bottom panel).

Figure 6A:
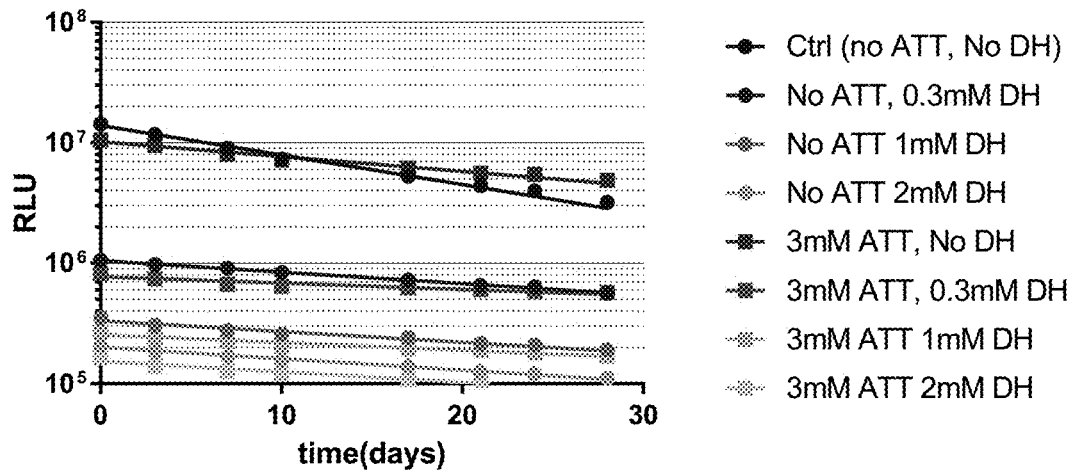
FIG. 6A shows the representative activities of luciferin substrate over time in the presence and absence of ATT at 37° C.
Figure 6B:
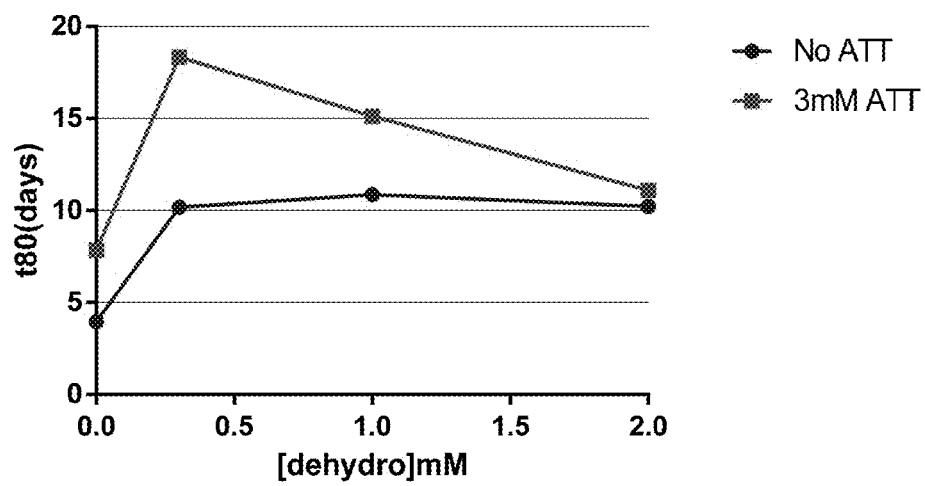
FIG. 6B shows the representative effect of ATT on the $T_{80}$ value of the luciferin substrate, measured at various concentrations of the corresponding dehydro-compound at 37° C.

In addition, it was shown that the addition of ATT (with or without the addition of dehydroluciferin) to Ultra-Glo™-based ATP detection reagent, which includes the Ultra-Glo™ enzyme, luciferin substrates, detergents for cell lysis, and other components in buffer, e.g. buffers containing various cationic detergents at pH 6.0, improved the complete reagent thermal stability at 37° C. (FIG. 6). $T_{80}$ (the storage time during which the complete ATP detection reagent produced ≥80% of the light output from the freshly made reagent), a parameter reflecting reagent thermal stability, was improved by 1 fold at 37° C. after addition of ATT. In particular, the $T_{80}$ value in the absence of ATT (0 mM) was 4 days, whereas the $T_{80}$ value in the presence of ATT (3 mM) was 8 days (FIG. 6A). Further, the combination of dehydroluciferin and ATT as additives further improved the reagent stability, increasing the $T_{80}$ value to 18 days (FIG. 6B, at 3 mM ATT with 0.3 mM corresponding dehydrocompound). Thus, the thionucleotide compounds as disclosed herein did not interfere with the bioluminescence analysis systems, which include luminescence enzymes and luciferin analogs. Instead, the thionucleotide compounds improved the stability of the luciferin analogs, which in turn improved the signal of the bioluminescence analysis over an extended period of time as compared to systems without such compounds.

6. CLAUSES

For reasons of completeness, various aspects of the invention are set out in the following numbered clauses:

Clause 1. A composition comprising
(a) a benzothiazole luciferin analog, or salt thereof; and
(b) an effective amount of a compound of formula (I) or a tautomer thereof,

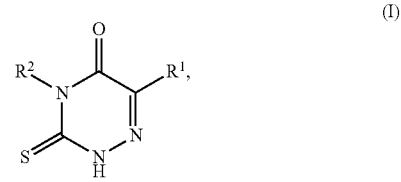

wherein
R¹ is hydrogen, optionally substituted alkyl, optionally substituted arylalkyl, optionally substituted heteroarylalkyl, optionally substituted cycloalkyl, optionally substituted aryl, optionally substituted heteroaryl, carboxylic acid, ester, $NR^aR^b$, optionally substituted imine, hydroxyl, or oxo;
R² is hydrogen, $NR^aR^b$, optionally substituted imine, optionally substituted alkyl, or optionally substituted aryl;
$R^a$ and $R^b$, at each occurrence, are each independently hydrogen, optionally substituted alkyl, or optionally substituted aryl; and
(c) optionally, a liquid medium
wherein when the liquid medium is absent, the benzothiazole luciferin analog and the compound of formula (I) form a solid mixture;
wherein when the liquid medium is present, and when the compound of formula (I) is 6-methyl-3-thioxo-3,4-dihydro-1,2,4-triazin-5(2H)-one (ATT), the liquid medium is free of dimethyl sulfoxide (DMSO).

Clause 2. The composition of clause 1, wherein the benzothiazole luciferin analog is a compound of formula (II')

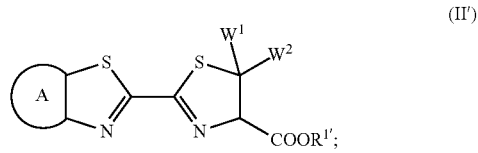

wherein:

A is

(a)
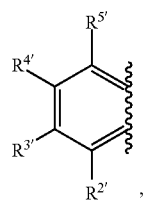, (b)
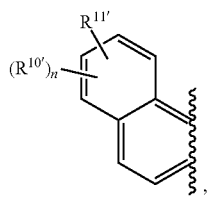, (c)
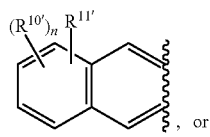, or (d)
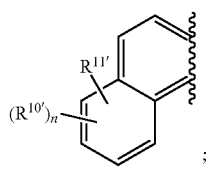;

$R^{1'}$ is H, $C_1$-$C_4$alkyl, —$C_2$-$C_4$alkylene-OH, —$C_2$-$C_4$alkylene-O$C_1$-$C_4$alkyl, $C_3$-$C_7$cycloalkyl, aryl, benzyl or substituted benzyl, heterocyclyl, heteroaryl, or —(CH$_2$)$_q$—P(Ph)$_3$, wherein q is an integer selected from 1, 2, 3, 4, 5, and 6;

$R^{2'}$ is hydrogen, halogen, $C_1$-$C_4$alkyl, or $C_1$-$C_4$haloalkyl;

$R^{3'}$ is hydrogen, halogen, $C_1$-$C_4$alkyl, or $C_1$-$C_4$haloalkyl;

$R^{4'}$ is —XG or —XG$^1$;

$R^{5'}$ is hydrogen, halogen, $C_1$-$C_4$alkyl, or $C_1$-$C_4$haloalkyl;

$R^{10'}$, at each occurrence is independently halo, —SO$_3$H, $C_1$-$C_{10}$alkyl, —OH, —O($C_1$-$C_{10}$alkyl), —NH$_2$, —NH($C_1$-$C_{10}$alkyl), or —N($C_1$-$C_{10}$alkyl)($C_1$-$C_{10}$alkyl);

$R^{11'}$ is —OH, —O($C_1$-$C_{10}$alkyl), —NH$_2$, —NH($C_1$-$C_{10}$alkyl), —N($C_1$-$C_{10}$alkyl)($C_1$-$C_{10}$alkyl), —OG$^1$, —NHG$^1$, or —N($C_1$-$C_{10}$alkyl)G$^1$;

n is 0 to 5;

X is —O— or —N(G)-;

G, at each occurrence is independently H, $C_1$-$C_{12}$alkyl, or together with one of $R^{3'}$ or $R^{5'}$ forms a 5- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl); or two G together with the nitrogen atom to which they are attached form a 4- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl);

G$^1$ comprises an enzyme substrate, wherein biotransformation of the enzyme substrate by an enzyme converts G$^1$ to H; and W$^1$ and W$^2$ are each independently hydrogen, $C_1$-$C_4$alkyl, or arylalkyl; or W$^1$ and W$^2$ together with the carbon to which they are attached form a $C_3$-$C_8$cycloalkyl or a 4- to 8-membered heterocycle, the cycloalkyl and heterocycle being optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl).

Clause 3. The composition of clause 1 or 2, wherein W$^1$ and W$^2$ are each independently $C_1$-$C_4$alkyl.

Clause 4. The composition of clause 1 or 2, wherein the benzothiazole luciferin analog is a compound of formula (II)

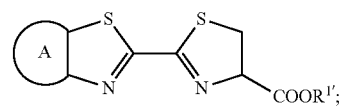
(II)

wherein:

A is

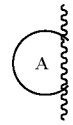

(a)
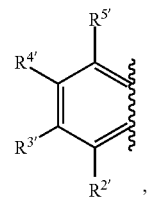, (b)
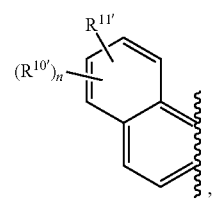, (c)
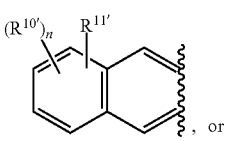, or

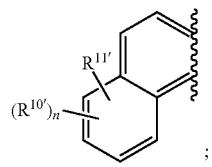
(d)

R[1'] is H, $C_1$-$C_4$alkyl, —$C_2$-$C_4$alkylene-OH, —$C_2$-$C_4$alkylene-O$C_1$-$C_4$alkyl, $C_3$-$C_7$cycloalkyl, aryl, benzyl or substituted benzyl, heterocyclyl, heteroaryl, or —$(CH_2)_q$—P(Ph)$_3$, wherein q is an integer selected from 1, 2, 3, 4, 5, and 6;

R[2'] is hydrogen, halogen, methyl, or trifluoromethyl;
R[3'] is hydrogen, halogen, methyl, or trifluoromethyl;
R[4'] is —XG or —XG[1];
R[5'] is hydrogen, halogen, methyl, or trifluoromethyl;
R[10'], at each occurrence is independently halo, —SO$_3$H, $C_1$-$C_{10}$alkyl, —OH, —O($C_1$-$C_{10}$alkyl), —NH$_2$, —NH($C_1$-$C_{10}$alkyl), or —N($C_1$-$C_{10}$alkyl)($C_1$-$C_{10}$alkyl);
R[11'] is —OH, —O($C_1$-$C_{10}$alkyl), —NH$_2$, —NH($C_1$-$C_{10}$alkyl), —N($C_1$-$C_{10}$alkyl)($C_1$-$C_{10}$alkyl), —OG[1], —NHG[1], or —N($C_1$-$C_{10}$alkyl)G[1];
n is 0 to 5;
X is —O— or —N(G)-;
G, at each occurrence is independently H, $C_1$-$C_{12}$alkyl, or together with one of R[3'] or R[5'] forms a 5- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl); or two G together with the nitrogen atom to which they are attached form a 4- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl); and
G[1] comprises an enzyme substrate, wherein biotransformation of the enzyme substrate by an enzyme converts G[1] to H.

Clause 5. The composition of any of clauses 1-4, wherein the composition does not contain a luminogenic enzyme.

Clause 6. The composition of any of clauses 1-5, wherein the benzothiazole luciferin analog is stabilized against decomposition.

Clause 7. The composition of clause 6, wherein the benzothiazole luciferin analog is stabilized against decomposition as compared to a composition that does not include the compound of formula (I) or tautomer thereof.

Clause 8. The composition of clause 6 or 7, wherein the benzothiazole luciferin analog is stabilized against decomposition in the presence of light.

Clause 9. The composition of clause 6 or 7, wherein the benzothiazole luciferin analog is stabilized against decomposition in the absence of light.

Clause 10. The composition of claim any of clauses 6-9, wherein benzothiazole luciferin analog is stabilized against decomposition at temperatures from −80° C. to 60° C.

Clause 11. The composition of any of clauses 2-10, wherein R[1'] is H.

Clause 12. The composition of any of clauses 2-11, wherein R[2'] is H, R[3'] is H, and R[5'] is H.

Clause 13. The composition of any of clauses 6-12, wherein the benzothiazole luciferin analog is stabilized against decomposition in the presence of light as compared to a composition that does not include the compound of formula (I) or tautomer thereof.

Clause 14. The composition of any of clauses 6-12, wherein the benzothiazole luciferin analog is stabilized against decomposition in the absence of light as compared to a composition that does not include the compound of formula (I) or tautomer thereof.

Clauses 15. The composition of any of clauses 2-14, wherein R[4'] is —OH or —NH$_2$.

Clause 16. The composition of any of clauses 1-15, wherein the effective amount of the compound of formula (I) is greater than 0.1 mM.

Clause 17. The composition of clause 16, wherein the effective amount of the compound of formula (I) is greater than 1 mM.

Clause 18. The composition of any of clauses 1-17, wherein the compound of formula (I) is selected from the group consisting of: ATT, ATCA, 3-(4-Amino-5-oxo-3-thioxo-2,3,4,5-tetrahydro-1,2,4-triazin-6-yl)propanoic acid, tetrahydro-2-methyl-3-thioxo-1,2,4-triazine-5,6-dione, 4-((2-furylmethylene)amino)-3-mercapto-6-methyl-1,2,4-triazin-5(4H)-one, 6-benzyl-3-sulfanyl-1,2,4-triazin-5-ol, 4-amino-3-mercapto-6-methyl-1,2,4-triazin-5(4H)-one, 3-(5-oxo-3-thioxo-2,3,4,5-tetrahydro-1,2,4-triazin-6-yl)propanoic acid, (E)-6-methyl-4-((thiophen-2-ylmethylene) amino)-3-thioxo-3,4-dihydro-1,2,4-triazin-5 (2H)-one, (E)-6-methyl-4-((3-nitrobenzylidene)amino)-3-thioxo-3,4-dihydro-1,2,4-triazin-5(2H)-one, (E)-4-((4-(diethylamino) benzylidene)amino)-6-methyl-3-thioxo-3,4-dihydro-1,2,4-triazin-5 (2H)-one, ATCA ethyl ester, TAK-0014, TAK-0002, TAK-0021, TAK-0020, TAK-0018, TAK-0009, TAK-0007, TAK-0008, TAK-0003, TAK-0004, 3-thioxo-6-(trifluoromethyl)-3,4-dihydro-1,2,4-triazin-5(2H)-one, 6-cyclopropyl-3-thioxo-3,4-dihydro-1,2,4-triazin-5(2H)-one, and 6-(hydroxymethyl)-3-thioxo-3,4-dihydro-1,2,4-triazin-5(2H)-one.

Clause 19. The composition of any of clauses 1-18, wherein the liquid medium is absent.

Clause 20. The composition of any of clauses 1-18, wherein the liquid medium is present.

Clause 21. The composition of clause 20, wherein the compound of formula (I) is not ATT.

Clause 22. The composition of clause 21, wherein the liquid medium comprises an organic solvent selected from the group consisting of alcohol, propylene glycol, dimethyl sulfoxide (DMSO), acetonitrile, glycerol, and any combination thereof.

Clause 23. The composition of clause 20, wherein the compound of formula (I) is ATT, and wherein the liquid medium comprises an organic solvent selected from the group consisting of alcohol, propylene glycol, acetonitrile, glycerol, and any combination thereof.

Clause 24. A method for stabilizing a benzothiazole luciferin analog, the method comprising contacting a benzothiazole luciferin analog, or salt thereof, with an effective amount of a compound of formula (I) or a tautomer thereof, whereby the benzothiazole luciferin analog, or salt thereof, is stabilized against decomposition,
wherein the compound of formula (I) is

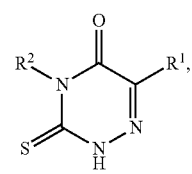
(I)

wherein

R¹ is hydrogen, optionally substituted alkyl, optionally substituted arylalkyl, optionally substituted heteroarylalkyl, optionally substituted cycloalkyl, optionally substituted aryl, optionally substituted heteroaryl, carboxylic acid, ester, $NR^aR^b$, optionally substituted imine, hydroxyl, or oxo;

R² is hydrogen, $NR^aR^b$, optionally substituted imine, optionally substituted alkyl, or optionally substituted aryl; and $R^a$ and $R^b$, at each occurrence, are each independently hydrogen, optionally substituted alkyl, or optionally substituted aryl.

Clause 25. The method of clause 24, wherein the benzothiazole luciferin analog is a compound of formula (II')

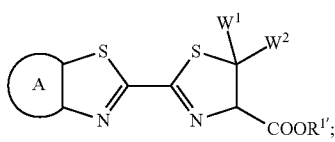
(II')

wherein:

A
is

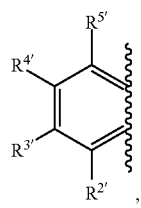
(a)

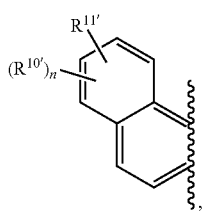
(b)

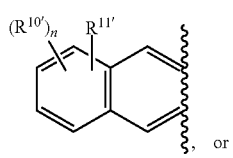
(c)

or

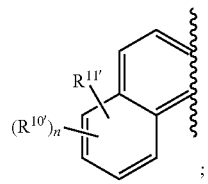
(d)

;

R¹' is H, $C_1$-$C_4$alkyl, —$C_2$-$C_4$alkylene-OH, —$C_2$-$C_4$alkylene-O$C_1$-$C_4$alkyl, $C_3$-$C_7$cycloalkyl, aryl, benzyl or substituted benzyl, heterocyclyl, heteroaryl, or —$(CH_2)_q$—$P(Ph)_3$, wherein q is an integer selected from 1, 2, 3, 4, 5, and 6;

R²' is hydrogen, halogen, methyl, or trifluoromethyl;

R³' is hydrogen, halogen, methyl, or trifluoromethyl;

R⁴' is —XG or —XG¹;

R⁵' is hydrogen, halogen, methyl, or trifluoromethyl;

$R^{10'}$, at each occurrence is independently halo, —$SO_3H$, $C_1$-$C_{10}$alkyl, —OH, —O($C_1$-$C_{10}$alkyl), —$NH_2$, —NH($C_1$-$C_{10}$alkyl), or —N($C_1$-$C_{10}$alkyl)($C_1$-$C_{10}$alkyl);

$R^{11'}$ is —OH, —O($C_1$-$C_{10}$alkyl), —$NH_2$, —NH($C_1$-$C_{10}$alkyl), —N($C_1$-$C_{10}$alkyl)($C_1$-$C_{10}$alkyl), —OG¹, —NHG¹, or —N($C_1$-$C_{10}$alkyl)G¹;

n is 0 to 5;

X is —O— or —N(G)-;

G, at each occurrence is independently H, $C_1$-$C_{12}$alkyl, or together with one of R³' or R⁵' forms a 5- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl); or two G together with the nitrogen atom to which they are attached form a 4- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl);

G¹ comprises an enzyme substrate, wherein biotransformation of the enzyme substrate by an enzyme converts G¹ to H; and W¹ and W² are each independently hydrogen, $C_1$-$C_4$alkyl, or arylalkyl; or W¹ and W² together with the carbon to which they are attached form a $C_3$-$C_8$cycloalkyl or a 4- to 8-membered heterocycle, the cycloalkyl and heterocycle being optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl).

Clause 26. The method of clause 24 or 25, wherein W¹ and W² are each independently $C_1$-$C_4$alkyl.

Clause 27. The method of clause 24 or 25, wherein the benzothiazole luciferin analog is a compound of formula (II)

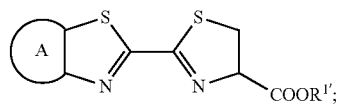
(II)

wherein:

is

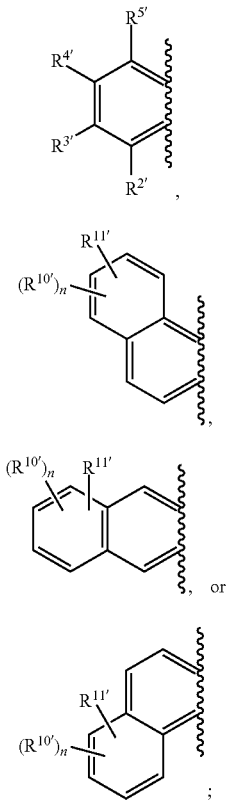

R$^{1'}$ is H, C$_1$-C$_4$alkyl, —C$_2$-C$_4$alkylene-OH, —C$_2$-C$_4$alkylene-OC$_1$-C$_4$alkyl, C$_3$-C$_7$cycloalkyl, aryl, benzyl or substituted benzyl, heterocyclyl, heteroaryl, or —(CH$_2$)$_q$—P(Ph)$_3$, wherein q is an integer selected from 1, 2, 3, 4, 5, and 6;
R$^{2'}$ is hydrogen, halogen, methyl, or trifluoromethyl;
R$^{3'}$ is hydrogen, halogen, methyl, or trifluoromethyl;
R$^{4'}$ is —XG or —XG$^1$;
R$^{5'}$ is hydrogen, halogen, methyl, or trifluoromethyl;
R$^{10'}$, at each occurrence is independently halo, —SO$_3$H, C$_1$-C$_{10}$alkyl, —OH, —O(C$_1$-C$_{10}$alkyl), —NH$_2$, —NH(C$_1$-C$_{10}$alkyl), or —N(C$_1$-C$_{10}$alkyl)(C$_1$-C$_{10}$alkyl);
R$^{11'}$ is —OH, —O(C$_1$-C$_{10}$alkyl), —NH$_2$, —NH(C$_1$-C$_{10}$alkyl), —N(C$_1$-C$_{10}$alkyl)(C$_1$-C$_{10}$alkyl), —OG$^1$, —NHG$^1$, or —N(C$_1$-C$_{10}$alkyl)G$^1$;
n is 0 to 5;
X is —O— or —N(G)-;
G, at each occurrence is independently H, C$_1$-C$_{12}$alkyl, or together with one of R$^{3'}$ or R$^{5'}$ forms a 5- to 8-membered monocyclic heterocyclic ring optionally substituted with 1-4 substituents independently selected from the group consisting of C$_1$-C$_4$alkyl, C$_1$-C$_4$haloalkyl, halo, hydroxy, oxo, and —O(C$_1$-C$_4$alkyl); or two G together with the nitrogen atom to which they are attached form a 4- to 8-membered monocyclic heterocyclic ring optionally substituted with 1-4 substituents independently selected from the group consisting of C$_1$-C$_4$alkyl, C$_1$-C$_4$haloalkyl, halo, hydroxy, oxo, and —O(C$_1$-C$_4$alkyl); and
G$^1$ comprises an enzyme substrate, wherein biotransformation of the enzyme substrate by an enzyme converts G$^1$ to H.

Clause 28. The method of any of clauses 24-27, wherein the effective amount of the compound of formula (I) is greater than 0.1 mM.

Clause 29. The method of clause 28, wherein the effective amount of the compound of formula (I) is greater than 1 mM.

Clause 30. The method of any of clauses 24-29, wherein the compound of formula (I) is selected from the group consisting of: ATT, ATCA, 3-(4-Amino-5-oxo-3-thioxo-2,3,4,5-tetrahydro-1,2,4-triazin-6-yl)propanoic acid, tetrahydro-2-methyl-3-thioxo-1,2,4-triazine-5,6-dione, 4-((2-furylmethylene)amino)-3-mercapto-6-methyl-1,2,4-triazin-5(4H)-one, 6-benzyl-3-sulfanyl-1,2,4-triazin-5-ol, 4-amino-3-mercapto-6-methyl-1,2,4-triazin-5(4H)-one, 3-(5-oxo-3-thioxo-2,3,4,5-tetrahydro-1,2,4-triazin-6-yl)propanoic acid, (E)-6-methyl-4-((thiophen-2-ylmethylene)amino)-3-thioxo-3,4-dihydro-1,2,4-triazin-5 (2H)-one, (E)-6-methyl-4-((3-nitrobenzylidene)amino)-3-thioxo-3,4-dihydro-1,2,4-triazin-5(2H)-one, (E)-4-((4-(diethylamino)benzylidene)amino)-6-methyl-3-thioxo-3,4-dihydro-1,2,4-triazin-5 (2H)-one, ATCA ethyl ester, TAK-0014, TAK-0002, TAK-0021, TAK-0020, TAK-0018, TAK-0009, TAK-0007, TAK-0008, TAK-0003, TAK-0004, 3-thioxo-6-(trifluoromethyl)-3,4-dihydro-1,2,4-triazin-5(2H)-one, 6-cyclopropyl-3-thioxo-3,4-dihydro-1,2,4-triazin-5(2H)-one, and 6-(hydroxymethyl)-3-thioxo-3,4-dihydro-1,2,4-triazin-5(2H)-one.

Clause 31. The method of any of clauses 24-30, wherein the benzothiazole luciferin analog is stabilized against decomposition in the presence of light.

Clause 32. The method of any of clauses 24-30, wherein the benzothiazole luciferin analog is stabilized against decomposition in the absence of light.

Clause 33. The method of any of clauses 24-32, wherein the luciferin analog is stabilized against decomposition at temperatures from −80° C. to 60° C.

Clause 34. The method of any of clauses 25-33, wherein R$^{1'}$ is H, R$^{2'}$ is H, R$^{3'}$ is H, and R$^{5'}$ is H.

Clause 35. The method of any of clauses 25-34, wherein R$^{4'}$ is —OH or —NH$_2$.

Clause 36. The method of any of clauses 24-35, wherein the contacting occurs in a solid mixture of the benzothiazole luciferin analog and the compound of formula (I).

Clause 37. The method of any of clauses 24-35, wherein the contacting occurs in a liquid medium.

Clause 38. The method of clause 37, wherein the compound of formula (I) is not ATT.

Clause 39. The method of clause 38, wherein the liquid medium comprises an organic solvent selected from the group consisting of alcohol, propylene glycol, dimethyl sulfoxide (DMSO), acetonitrile, glycerol, and any combination thereof.

Clause 40. The method of clause 37 wherein the compound of formula (I) is ATT, and wherein the liquid medium comprises an organic solvent selected from the group consisting of alcohol, propylene glycol, acetonitrile, glycerol, and any combination thereof.

Clause 41. A kit comprising the composition of any of clauses 1-23 in a single container, wherein the compound of formula (I) stabilizes the benzothiazole luciferin analog.

Clause 42. The kit of clause 41, wherein $R^{1'}$ is H, $R^{2'}$ is H, $R^{3'}$ is H, and $R^{5'}$ is H.

Clause 43. The kit of clause 41 or 42, wherein $R^{4'}$ is —OH or —NH$_2$.

Clause 44. The kit of any of clauses 41-43, wherein the effective amount of the compound of formula (I) is greater than 0.1 mM.

Clause 45. The kit of clause 44, wherein the effective amount of the compound of formula (I) is greater than 1 mM.

Clause 46. The kit of any of clauses 41-45, wherein the compound of formula (I) is selected from the group consisting of: ATT, ATCA, 3-(4-Amino-5-oxo-3-thioxo-2,3,4,5-tetrahydro-1,2,4-triazin-6-yl)propanoic acid, tetrahydro-2-methyl-3-thioxo-1,2,4-triazine-5,6-dione, 4-((2-furylmethylene)amino)-3-mercapto-6-methyl-1,2,4-triazin-5(4H)-one, 6-benzyl-3-sulfanyl-1,2,4-triazin-5-ol, 4-amino-3-mercapto-6-methyl-1,2,4-triazin-5(4H)-one, 3-(5-oxo-3-thioxo-2,3,4,5-tetrahydro-1,2,4-triazin-6-yl)propanoic acid, (E)-6-methyl-4-((thiophen-2-ylmethylene)amino)-3-thioxo-3,4-dihydro-1,2,4-triazin-5 (2H)-one, (E)-6-methyl-4-((3-nitrobenzylidene)amino)-3-thioxo-3,4-dihydro-1,2,4-triazin-5(2H)-one, (E)-4-((4-(diethylamino)benzylidene)amino)-6-methyl-3-thioxo-3,4-dihydro-1,2,4-triazin-5 (2H)-one, ATCA ethyl ester, TAK-0014, TAK-0002, TAK-0021, TAK-0020, TAK-0018, TAK-0009, TAK-0007, TAK-0008, TAK-0003, TAK-0004, 3-thioxo-6-(trifluoromethyl)-3,4-dihydro-1,2,4-triazin-5(2H)-one, 6-cyclopropyl-3-thioxo-3,4-dihydro-1,2,4-triazin-5(2H)-one, and 6-(hydroxymethyl)-3-thioxo-3,4-dihydro-1,2,4-triazin-5(2H)-one.

Clause 47. The kit of any of clauses 41-46, wherein the liquid medium is absent.

Clause 48. The kit of any of clauses 41-46, wherein the liquid medium is present.

Clause 49. The kit of clause 48, wherein the compound of formula (I) is not ATT.

Clause 50. The kit of clause 49, wherein the liquid medium comprises an organic solvent selected from the group consisting of alcohol, propylene glycol, dimethyl sulfoxide (DMSO), acetonitrile, glycerol, and any combination thereof.

Clause 51. The kit of clause 48, wherein the compound of formula (I) is ATT, and wherein the liquid medium comprises an organic solvent selected from the group consisting of alcohol, propylene glycol, acetonitrile, glycerol, and any combination thereof.

What is claimed is:

1. A composition comprising
   (a) a benzothiazole luciferin analog, or salt thereof, wherein the benzothiazole luciferin analog is a compound of formula (II')

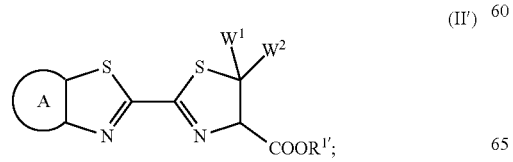

(II')

wherein:

is

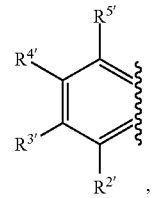 (a)

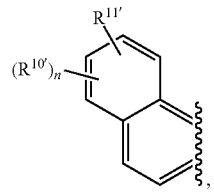 (b)

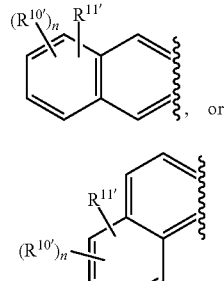 (c), or

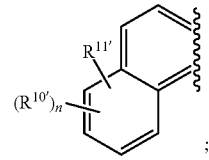 (d)

$R^{1'}$ is H, $C_1$-$C_4$alkyl, —$C_2$-$C_4$alkylene-OH, —$C_2$-$C_4$alkylene-O$C_1$-$C_4$alkyl, $C_3$-$C_7$cycloalkyl, aryl, benzyl or substituted benzyl, heterocyclyl, heteroaryl, or —(CH$_2$)$_q$—P(Ph)$_3$, wherein q is an integer selected from 1, 2, 3, 4, 5, and 6;

$R^{2'}$ is hydrogen, halogen, $C_1$-$C_4$alkyl, or $C_1$-$C_4$haloalkyl;

$R^{3'}$ is hydrogen, halogen, $C_1$-$C_4$alkyl, or $C_1$-$C_4$haloalkyl;

$R^{4'}$ is —XG or —XG$^1$;

$R^{5'}$ is hydrogen, halogen, $C_1$-$C_4$alkyl, or $C_1$-$C_4$haloalkyl;

$R^{10'}$, at each occurrence is independently halo, —SO$_3$H, $C_1$-$C_{10}$alkyl, —OH, —O($C_1$-$C_{10}$alkyl), —NH$_2$, —NH($C_1$-$C_{10}$alkyl), or —N($C_1$-$C_{10}$alkyl)($C_1$-$C_{10}$alkyl);

$R^{11'}$ is —OH, —O($C_1$-$C_{10}$alkyl), —NH$_2$, —NH($C_1$-$C_{10}$alkyl), —N($C_1$-$C_{10}$alkyl)($C_1$-$C_{10}$alkyl), —OG$^1$, —NHG$^1$, or —N($C_1$-$C_{10}$alkyl)G$^1$;

n is 0 to 5;

X is —O— or —N(G)-;

G, at each occurrence is independently H, $C_1$-$C_{12}$alkyl, or together with one of $R^{3'}$ or $R^{5'}$ forms a 5- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl); or two G together with the nitrogen atom to which they are attached form a 4- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl);

$G^1$ comprises an enzyme substrate, wherein biotransformation of the enzyme substrate by an enzyme converts $G^1$ to H; and $W^1$ and $W^2$ are each independently hydrogen, $C_1$-$C_4$alkyl, or arylalkyl; or $W^1$ and $W^2$ together with the carbon to which they are attached form a $C_3$-$C_8$cycloalkyl or a 4- to 8-membered heterocycle, the cycloalkyl and heterocycle being optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl); and (b) an effective amount of a compound of formula (I) or a tautomer thereof,

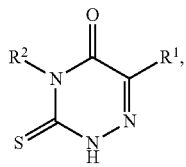

(I)

wherein
$R^1$ is hydrogen, optionally substituted alkyl, optionally substituted arylalkyl, optionally substituted heteroarylalkyl, optionally substituted cycloalkyl, optionally substituted aryl, optionally substituted heteroaryl, carboxylic acid, ester, $NR^aR^b$, optionally substituted imine, hydroxyl, or oxo;

$R^2$ is hydrogen, $NR^aR^b$, optionally substituted imine, optionally substituted alkyl, or optionally substituted aryl;

$R^a$ and $R^b$, at each occurrence, are each independently hydrogen, optionally substituted alkyl, or optionally substituted aryl; and (c) optionally, a liquid medium wherein when the liquid medium is absent, the benzothiazole luciferin analog and the compound of formula (I) form a solid mixture;

wherein when the liquid medium is present, and when the compound of formula (I) is 6-methyl-3-thioxo-3,4-dihydro-1,2,4-triazin-5(2H)-one (ATT), the liquid medium is free of dimethyl sulfoxide (DMSO).

2. The composition of claim 1, wherein $W^1$ and $W^2$ are each independently $C_1$-$C_4$alkyl.

3. The composition of claim 1, wherein the benzothiazole luciferin analog is a compound of formula (II)

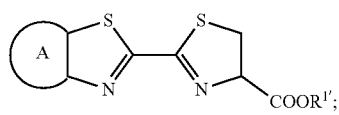

(II)

wherein:

is

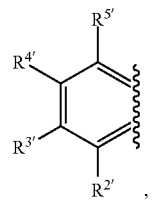

(a)

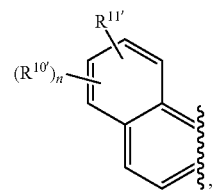

(b)

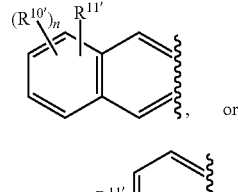

(c)

, or

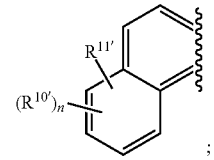

(d)

;

$R^{1'}$ is H, $C_1$-$C_4$alkyl, —$C_2$-$C_4$alkylene-OH, —$C_2$-$C_4$alkylene-O$C_1$-$C_4$alkyl, $C_3$-$C_7$cycloalkyl, aryl, benzyl or substituted benzyl, heterocyclyl, heteroaryl, or —$(CH_2)_q$—$P(Ph)_3$, wherein q is an integer selected from 1, 2, 3, 4, 5, and 6;

$R^{2'}$ is hydrogen, halogen, methyl, or trifluoromethyl;
$R^{3'}$ is hydrogen, halogen, methyl, or trifluoromethyl;
$R^{4'}$ is —XG or —X$G^1$;
$R^{5'}$ is hydrogen, halogen, methyl, or trifluoromethyl;
$R^{10'}$, at each occurrence is independently halo, —$SO_3H$, $C_1$-$C_{10}$alkyl, —OH, —O($C_1$-$C_{10}$alkyl), —$NH_2$, —NH($C_1$-$C_{10}$alkyl), or —N($C_1$-$C_{10}$alkyl)($C_1$-$C_{10}$alkyl);
$R^{11'}$ is —OH, —O($C_1$-$C_{10}$alkyl), —$NH_2$, —NH($C_1$-$C_{10}$alkyl), —N($C_1$-$C_{10}$alkyl)($C_1$-$C_{10}$alkyl), —O$G^1$, —NH$G^1$, or —N($C_1$-$C_{10}$alkyl)$G^1$;
n is 0 to 5;
X is —O— or —N(G)-;
G, at each occurrence is independently H, $C_1$-$C_{12}$alkyl, or together with one of $R^{3'}$ or $R^{5'}$ forms a 5- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl); or two G together with the nitrogen atom to which they are attached form a 4- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl); and
$G^1$ comprises an enzyme substrate, wherein biotransformation of the enzyme substrate by an enzyme converts $G^1$ to H.

4. The composition of claim 1, wherein the composition does not contain a luminogenic enzyme.

5. The composition of claim 1, wherein the benzothiazole luciferin analog is stabilized against decomposition.

6. The composition of claim 1, wherein $R^{1'}$ is H.

7. The composition of claim 1, wherein $R^{2'}$ is H, $R^{3'}$ is H, and $R^{5'}$ is H.

8. The composition of claim 1, wherein $R^{4'}$ is —OH or —NH$_2$.

9. The composition of claim 1, wherein the effective amount of the compound of formula (I) is greater than 0.1 mM.

10. The composition of claim 1, wherein the compound of formula (I) is selected from the group consisting of: ATT, ATCA, 3-(4-Amino-5-oxo-3-thioxo-2,3,4,5-tetrahydro-1,2,4-triazin-6-yl)propanoic acid, tetrahydro-2-methyl-3-thioxo-1,2,4-triazine-5,6-dione, 4-((2-furylmethylene)amino)-3-mercapto-6-methyl-1,2,4-triazin-5(4H)-one, 6-benzyl-3-sulfanyl-1,2,4-triazin-5-ol, 4-amino-3-mercapto-6-methyl-1,2,4-triazin-5(4H)-one, 3-(5-oxo-3-thioxo-2,3,4,5-tetrahydro-1,2,4-triazin-6-yl)propanoic acid, (E)-6-methyl-4-((thiophen-2-ylmethylene)amino)-3-thioxo-3,4-dihydro-1,2,4-triazin-5 (2H)-one, (E)-6-methyl-4-((3-nitrobenzylidene)amino)-3-thioxo-3,4-dihydro-1,2,4-triazin-5(2H)-one, (E)-4-((4-(diethylamino)benzylidene)amino)-6-methyl-3-thioxo-3,4-dihydro-1,2,4-triazin-5 (2H)-one, ATCA ethyl ester, TAK-0014, TAK-0002, TAK-0021, TAK-0020, TAK-0018, TAK-0009, TAK-0007, TAK-0008, TAK-0003, TAK-0004, 3-thioxo-6-(trifluoromethyl)-3,4-dihydro-1,2,4-triazin-5(2H)-one, 6-cyclopropyl-3-thioxo-3,4-dihydro-1,2,4-triazin-5(2H)-one, and 6-(hydroxymethyl)-3-thioxo-3,4-dihydro-1,2,4-triazin-5(2H)-one.

11. The composition of claim 1, wherein the liquid medium is absent.

12. The composition of claim 1, wherein the liquid medium is present.

13. The composition of claim 12, wherein the compound of formula (I) is not ATT.

14. The composition of claim 13, wherein the liquid medium comprises an organic solvent selected from the group consisting of alcohol, propylene glycol, dimethyl sulfoxide (DMSO), acetonitrile, glycerol, and any combination thereof.

15. The composition of claim 12, wherein the compound of formula (I) is ATT, and wherein the liquid medium comprises an organic solvent selected from the group consisting of alcohol, propylene glycol, acetonitrile, glycerol, and any combination thereof.

16. A method for stabilizing a benzothiazole luciferin analog, the method comprising contacting a benzothiazole luciferin analog, or salt thereof, with an effective amount of a compound of formula (I) or a tautomer thereof, whereby the benzothiazole luciferin analog, or salt thereof, is stabilized against decomposition, wherein the benzothiazole luciferin analog is a compound of formula (II')

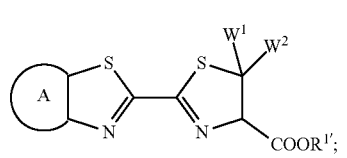

(II')

wherein:

is

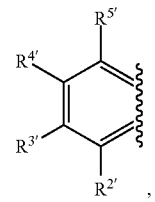 (a)

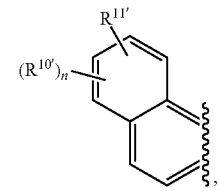 (b)

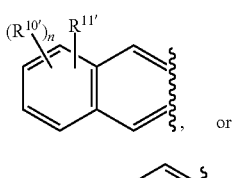 (c)

, or (d)

$R^{1'}$ is H, $C_1$-$C_4$alkyl, —$C_2$-$C_4$alkylene-OH, —$C_2$-$C_4$alkylene-O$C_1$-$C_4$alkyl, $C_3$-$C_7$cycloalkyl, aryl, benzyl or substituted benzyl, heterocyclyl, heteroaryl, or —(CH$_2$)$_q$—P(Ph)$_3$, wherein q is an integer selected from 1, 2, 3, 4, 5, and 6;

$R^{2'}$ is hydrogen, halogen, methyl, or trifluoromethyl;

$R^{3'}$ is hydrogen, halogen, methyl, or trifluoromethyl;

$R^{4'}$ is —XG or —XG$^1$;

$R^{5'}$ is hydrogen, halogen, methyl, or trifluoromethyl;

$R^{10'}$, at each occurrence is independently halo, —SO$_3$H, $C_1$-$C_{10}$alkyl, —OH, —O($C_1$-$C_{10}$alkyl), —NH$_2$, —NH($C_1$-$C_{10}$alkyl), or —N($C_1$-$C_{10}$alkyl)($C_1$-$C_{10}$alkyl);

$R^{11'}$ is —OH, —O($C_1$-$C_{10}$alkyl), —NH$_2$, —NH($C_1$-$C_{10}$alkyl), —N($C_1$-$C_{10}$alkyl)($C_1$-$C_{10}$alkyl), —OG$^1$, —NHG$^1$, or —N($C_1$-$C_{10}$alkyl)G$^1$;

n is 0 to 5;

X is —O— or —N(G)-;

G, at each occurrence is independently H, $C_1$-$C_{12}$alkyl, or together with one of $R^{3'}$ or $R^{5'}$ forms a 5- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl); or two G together with the nitrogen atom to which they are attached form a 4- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl);

$G^1$ comprises an enzyme substrate, wherein biotransformation of the enzyme substrate by an enzyme converts $G^1$ to H; and $W^1$ and $W^2$ are each independently hydrogen, $C_1$-$C_4$alkyl, or arylalkyl; or $W^1$ and $W^2$ together with the carbon to which they are attached form a $C_3$-$C_8$cycloalkyl or a 4- to 8-membered heterocycle, the cycloalkyl and heterocycle being optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl); and wherein the compound of formula (I) is

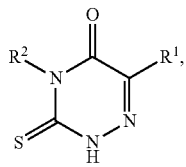
(I)

wherein
- $R^1$ is hydrogen, optionally substituted alkyl, optionally substituted arylalkyl, optionally substituted heteroarylalkyl, optionally substituted cycloalkyl, optionally substituted aryl, optionally substituted heteroaryl, carboxylic acid, ester, $NR^aR^b$, optionally substituted imine, hydroxyl, or oxo;
- $R^2$ is hydrogen, $NR^aR^b$, optionally substituted imine, optionally substituted alkyl, or optionally substituted aryl; and
- $R^a$ and $R^b$, at each occurrence, are each independently hydrogen, optionally substituted alkyl, or optionally substituted aryl.

17. The method of claim 16, wherein $W^1$ and $W^2$ are each independently $C_1$-$C_4$alkyl.

18. The method of claim 16, wherein the benzothiazole luciferin analog is a compound of formula (II)

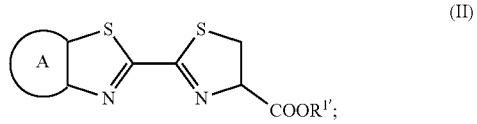
(II)

wherein:

is

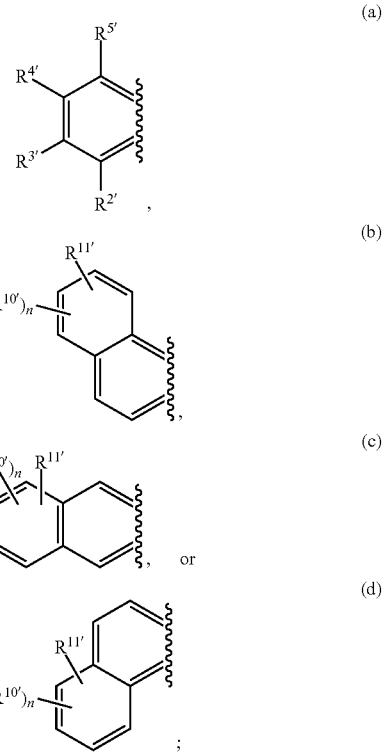

$R^{1'}$ is H, $C_1$-$C_4$alkyl, —$C_2$-$C_4$alkylene-OH, —$C_2$-$C_4$alkylene-O$C_1$-$C_4$alkyl, $C_3$-$C_7$cycloalkyl, aryl, benzyl or substituted benzyl, heterocyclyl, heteroaryl, or —$(CH_2)_q$—$P(Ph)_3$, wherein q is an integer selected from 1, 2, 3, 4, 5, and 6;

$R^{2'}$ is hydrogen, halogen, methyl, or trifluoromethyl;
$R^{3'}$ is hydrogen, halogen, methyl, or trifluoromethyl;
$R^{4'}$ is —XG or —$XG^1$;
$R^{5'}$ is hydrogen, halogen, methyl, or trifluoromethyl;
$R^{10'}$, at each occurrence is independently halo, —$SO_3H$, $C_1$-$C_{10}$alkyl, —OH, —O($C_1$-$C_{10}$alkyl), —$NH_2$, —NH($C_1$-$C_{10}$alkyl), or —N($C_1$-$C_{10}$alkyl)($C_1$-$C_{10}$alkyl);
$R^{11'}$ is —OH, —O($C_1$-$C_{10}$alkyl), —$NH_2$, —NH($C_1$-$C_{10}$alkyl), —N($C_1$-$C_{10}$alkyl)($C_1$-$C_{10}$alkyl), —$OG^1$, —$NHG^1$, or —N($C_1$-$C_{10}$alkyl)$G^1$;
n is 0 to 5;
X is —O— or —N(G)-;
G, at each occurrence is independently H, $C_1$-$C_{12}$alkyl, or together with one of $R^{3'}$ or $R^{5'}$ forms a 5- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl); or two G together with the nitrogen atom to which they are attached form a 4- to 8-membered monocyclic heterocyclic ring optionally substituted with 1-4 substituents independently selected from the group consisting of $C_1$-$C_4$alkyl, $C_1$-$C_4$haloalkyl, halo, hydroxy, oxo, and —O($C_1$-$C_4$alkyl); and
$G^1$ comprises an enzyme substrate, wherein biotransformation of the enzyme substrate by an enzyme converts $G^1$ to H.

19. The method of claim 16, wherein the effective amount of the compound of formula (I) is greater than 0.1 mM.

20. The method of claim 16, wherein the compound of formula (I) is selected from the group consisting of: ATT, ATCA, 3-(4-Amino-5-oxo-3-thioxo-2,3,4,5-tetrahydro-1,2,4-triazin-6-yl)propanoic acid, tetrahydro-2-methyl-3-thioxo-1,2,4-triazine-5,6-dione, 4-((2-furylmethylene)amino)-3-mercapto-6-methyl-1,2,4-triazin-5(4H)-one, 6-benzyl-3-sulfanyl-1,2,4-triazin-5-ol, 4-amino-3-mercapto-6-methyl-1,2,4-triazin-5(4H)-one, 3-(5-oxo-3-thioxo-2,3,4,5-tetrahydro-1,2,4-triazin-6-yl)propanoic acid, (E)-6-methyl-4-((thiophen-2-ylmethylene)amino)-3-thioxo-3,4-dihydro-1,2,4-triazin-5 (2H)-one, (E)-6-methyl-4-((3-nitrobenzylidene)amino)-3-thioxo-3,4-dihydro-1,2,4-triazin-5(2H)-one, (E)-4-((4-(diethylamino)benzylidene)amino)-6-methyl-3-thioxo-3,4-dihydro-1,2,4-triazin-5 (2H)-one, ATCA ethyl ester, TAK-0014, TAK-0002, TAK-0021, TAK-0020, TAK-0018, TAK-0009, TAK-0007, TAK-0008, TAK-0003, TAK-0004, 3-thioxo-6-(trifluoromethyl)-3,4-dihydro-1,2,4-triazin-5(2H)-one, 6-cyclopropyl-3-thioxo-3,4-dihydro-1,2,4-triazin-5(2H)-one, and 6-(hydroxymethyl)-3-thioxo-3,4-dihydro-1,2,4-triazin-5(2H)-one.

21. The method of claim 16, wherein the benzothiazole luciferin analog is stabilized against decomposition in the presence of light.

22. The method of claim 16, wherein the benzothiazole luciferin analog is stabilized against decomposition in the absence of light.

23. The method of claim 16, wherein the luciferin analog is stabilized against decomposition at temperatures from −80° C. to 60° C.

24. The method of claim 16, wherein $R^{1'}$ is H, $R^{2'}$ is H, $R^{3'}$ is H, and $R^{5'}$ is H.

25. The method of claim 16, wherein $R^{4'}$ is —OH or —NH$_2$.

26. The method of claim 16, wherein the contacting occurs in a solid mixture of the benzothiazole luciferin analog and the compound of formula (I).

27. The method of claim 16, wherein the contacting occurs in a liquid medium.

28. The method of claim 27, wherein the compound of formula (I) is not ATT.

29. The method of claim 28, wherein the liquid medium comprises an organic solvent selected from the group consisting of alcohol, propylene glycol, dimethyl sulfoxide (DMSO), acetonitrile, glycerol, and any combination thereof.

30. The method of claim 27 wherein the compound of formula (I) is ATT, and wherein the liquid medium comprises an organic solvent selected from the group consisting of alcohol, propylene glycol, acetonitrile, glycerol, and any combination thereof.

31. A kit comprising the composition of claim 1 in a single container, wherein the compound of formula (I) stabilizes the benzothiazole luciferin analog.

* * * * *